(12) United States Patent
Coleman et al.

(10) Patent No.: US 6,872,548 B2
(45) Date of Patent: Mar. 29, 2005

(54) SCAFFOLDED FUSION POLYPEPTIDES AND COMPOSITIONS AND METHODS FOR MAKING THE SAME

(75) Inventors: Timothy A. Coleman, Gaithersburg, MD (US); Brian C. Mansfield, Catonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 136 days.

(21) Appl. No.: 10/057,890

(22) Filed: Jan. 29, 2002

(65) Prior Publication Data

US 2003/0044901 A1 Mar. 6, 2003

Related U.S. Application Data

(60) Provisional application No. 60/265,782, filed on Jan. 31, 2001, and provisional application No. 60/265,858, filed on Jan. 31, 2001.

(51) Int. Cl.$^7$ .......................... C12P 21/00; C12N 5/02; C07K 17/00
(52) U.S. Cl. ...................... 435/69.1; 435/325; 530/350
(58) Field of Search ................................ 435/69.1, 325; 530/350

(56) References Cited

U.S. PATENT DOCUMENTS

| | | | |
|---|---|---|---|
| 5,196,510 A | | 3/1993 | Rodwell et al. |
| RE35,585 E | * | 8/1997 | Fernandez-Pol ............ 536/23.5 |
| 5,763,183 A | * | 6/1998 | Pesonen et al. ................. 435/6 |
| 5,789,538 A | * | 8/1998 | Rebar et al. ................. 530/324 |
| 5,821,067 A | * | 10/1998 | Grandy et al. ................ 435/7.2 |
| 5,837,809 A | * | 11/1998 | Grandy et al. ................ 530/326 |
| 5,861,495 A | * | 1/1999 | Hillman et al. ............. 536/23.1 |
| 5,905,146 A | * | 5/1999 | Lecka-Czernik ............ 536/23.5 |
| 5,928,955 A | | 7/1999 | Imperiali et al. |
| 5,948,890 A | * | 9/1999 | Soppet et al. ................ 530/350 |
| 5,981,223 A | * | 11/1999 | Sathe et al. ................. 435/69.1 |
| 6,007,988 A | * | 12/1999 | Choo et al. ..................... 435/6 |
| 6,010,877 A | * | 1/2000 | Sathe et al. ................. 435/69.1 |
| 6,534,261 B1 | * | 3/2003 | Cox et al. ....................... 435/6 |
| 2002/0137891 A1 | * | 9/2002 | Hill et al. .................... 530/350 |

OTHER PUBLICATIONS

MacLennan et al. (Aug. 1998) "Structure–function Relationships in the Ca2+–Binding and Translocation Domain of SERCA1: physiological correlates in Brody disease." Acta Physiol. Scand. 163: 55–67.*

Procyshyn & Reid (Jan. 21, 1994) "A Structure/Activity Study of Calcium Affinity and Selectivity Using a Synthetic Peptide Model of the Helix–Loop–Helix Calcium–binding Motif." The Journal of Biological Chemistry 269(3): 1641–1647.*

Raport et al. (Jul. 19, 1996) "Molecular Cloning and Functional Characterization of a Novel Human CC Chemokine Receptor (CCR5) for RANTES, MIP–1b, and MIP–1a." The Journal of Biological Chemistry 271(29): 17161–17166.*

Ling et al. (Jul. 1999) "Five–transmembrane domains appear sufficient for a G protein–coupled receptor: Functional five–transmembrane domain chemokine receptors." PNAS 96: 7922–7927.*

(Continued)

Primary Examiner—Elizabeth Kemmerer
Assistant Examiner—Christopher James Nichols
(74) Attorney, Agent, or Firm—Human Genome Sciences, Inc.

(57) ABSTRACT

The present invention provides soluble forms of integral membrane proteins, or domains or portions thereof, that retain the biological activity of the integral membrane protein, domain or portion from which they are designed or derived and that can readily be expressed in high yield.

3 Claims, 4 Drawing Sheets

OTHER PUBLICATIONS

Figure 1B:
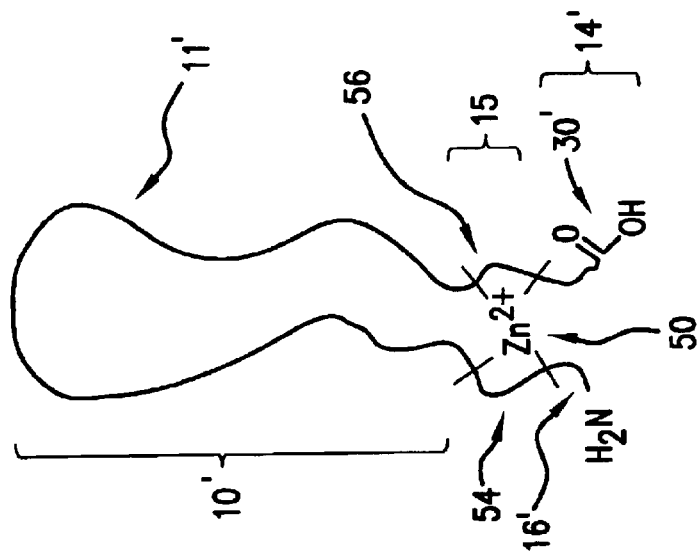

Choe et al. (Jun. 28, 1996) "The b–Chemokine Receptors CCR3 and CCR5 Facilitate Infection by Primary HIV–1 Isolates." Cell 85: 1135–1148.*

Howard et al. (Mar. 2001) "Orphan G–protein–coupled receptors and natural ligand discovery." TRENDS in Pharmocological Sciences 22(3): 132–140.*

Harrison et al. (Apr. 1999) "Copper chaperones: function, structure and copper–binding properties." J Biol Inorg Chem. 4(2): 145–153.*

Loomans et al. (Mar. 1998) "Histidine–based zinc–binding sequences and the antimicrobial activity of calprotectin." J Infect Di 177(3): 812–814.*

Rhoads & Friedburg (Apr. 1997) "Sequence motifs for calmodulin recognition." FASEB J. 11(5): 331–340.*

Hooper (Oct. 31, 1994) "Families of zinc metalloproteases." FEBS Lett. 354(1): 1–6.*

MacKenzie et al. (Aug. 1995) "Bifunctional fusion proteins consisting of a single–chain antibody and an engineered lanthanid binding protein." Immunotechnology 1(2): 139–150.*

Eng et al. (Nov. 1, 1998) "Sequence Analyses and Phylogentic Characterization of the ZIP Family of Metal Ion Transport Proteins." J. Membrane Biol. 166(1): 1–7.*

Lewit–Bentley & Réty (Dec. 2000) "EF–hand calcium–binding proteins." Current Opinion in Structural Biology 10(6): 637–643.*

Laity et al. (Feb. 2001) "Zinc finger proteins: new insights into structural and functional diversity." Current Opinion in Structural Biology 11(1): 39–46.*

Z. Wang et al., "CCR5 HIV–1 Coreceptor Activity Role of Cooperativity Between Residues in N–Terminal Extracellular and Intracellular Domains", J. of Biol. Chemistry 274(40):28413–28419 (1999).

* cited by examiner

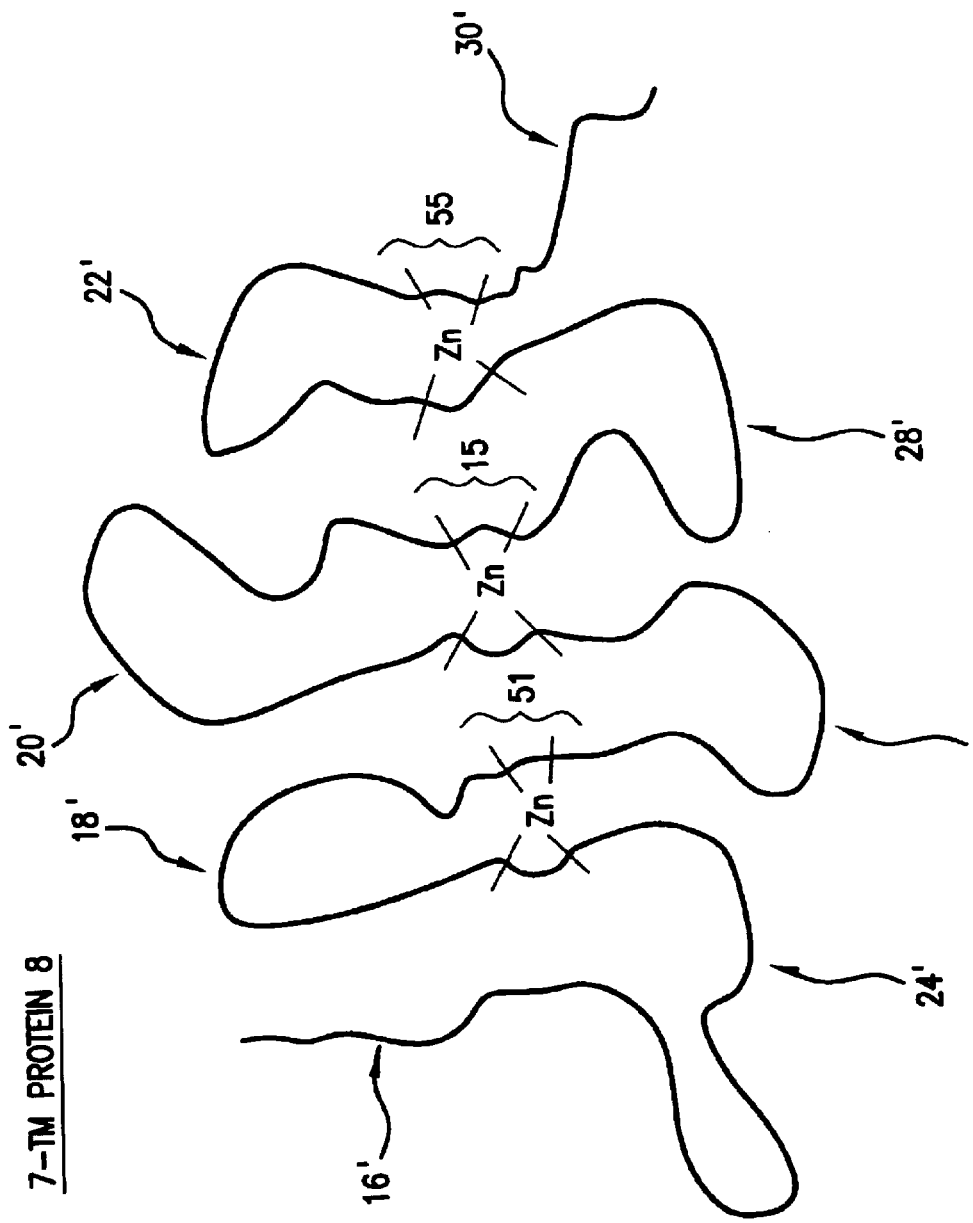

SCAFFOLDED FUSION POLYPEPTIDES AND COMPOSITIONS AND METHODS FOR MAKING THE SAME

This application claims benefit under 35 U.S.C. §119(e) based on the following U.S. Provisional Applications: Serial No. 60/265,782, filed Jan. 31, 2001, and Ser. No. 60/265,858, filed Jan. 31, 2001, both of which are hereby incorporated by reference in their entirety.

1. FIELD OF THE INVENTION

The present invention relates to novel compositions designed from integral membrane proteins that have improved solubility and retain biological activity.

2. BACKGROUND OF THE INVENTION

Many important cellular and biological processes are mediated by integral membrane proteins. Often quantities of these integral membrane proteins are required to study their roles in the critical cellular and biological processes. However, integral membrane proteins are often difficult to obtain in quantity while retaining solubility and function.

For example, according to one common technique, the integral membrane protein is extracted from the bilayer with a nonionic detergent. Unfortunately, the proteins recovered by such extraction techniques frequently lack activity.

In another common technique, a soluble portion of the membrane protein, such as an extracellular domain, is expressed in the absence of the insoluble portions of the membrane protein (typically the transmembrane region). However, this method is inadequate for expressing the soluble portions of many membrane proteins, especially those that traverse the membrane more than once. In such proteins that span the membrane more than once, the transmembrane domains and the lipid bilayer can be crucial to the proper folding of the soluble portion of the membrane protein.

New techniques are needed that provide quantities of integral membrane proteins, or domains or portions thereof, in a soluble and active form.

3. SUMMARY OF THE INVENTION

In one aspect, the present invention provides scaffolded fusion polypeptides designed from integral membrane proteins that display improved solubility in a membrane-free and detergent-free aqueous environment and that retain at least a portion of the biological activity of the integral membrane protein from which they were designed. In one embodiment, the scaffolded fusion polypeptide of the invention comprises a first scaffold strand, a second scaffold strand and a functional domain. The scaffold strands are fused to opposite ends of the functional domain, either directly or by way of a linker, and taken together constitute a scaffold domain.

The functional domain comprises a polypeptide having an amino acid sequence that corresponds to a region of a protein of interest believed or known to possess biological activity. In some embodiments of the invention, the functional domain of the scaffolded fusion polypeptide retains or mimics one or more functions of the region of the protein of interest to which it corresponds. In other embodiments of the invention, the functional domain retains none of the functions of the region of the protein of interest, but rather has unique functions of its own. Preferred functional domains retain or mimic one or more biological activities of the protein of interest. Particularly useful functional domains correspond to loops or strands of soluble domains of integral membrane proteins. For instance, integral membrane proteins, including receptors, often possess extracellular domains ("ECDs"), intracellular domains ("ICDs") and transmembrane domains ("TMDs"). Typically, the ECDs and ICDs of such proteins are referred to as the soluble domains, whereas the TMDs are referred to as the insoluble domains. The ECDs and/or ICDs may comprise a single loop or multiple loops, depending upon the number of times the integral membrane protein spans the membrane. Thus, particularly useful scaffolded fusion polypeptides include those in which the functional domain has an amino acid sequence that corresponds to the amino acid sequence of a loop of an ECD or an ICD of an integral membrane protein. Particularly useful scaffolded fusion polypeptides also correspond to soluble portions of integral membrane proteins that are not on the surface of a cell, including nuclear membrane proteins, mitochondrial membrane proteins, membrane proteins of the endoplasmic reticulum and other integral membrane proteins.

Taken together, the scaffold strands of the scaffolded fusion polypeptide constitute a scaffold domain. The scaffold domain mimics the TMD adjacent the ECD or ICD loop of the integral membrane protein from which the scaffolded fusion polypeptide of the invention is designed, with one significant difference. Whereas the TMDs of integral membrane proteins are hydrophobic in nature, thereby causing the integral membrane proteins to be insoluble in membrane-free and detergent-free aqueous medium, the scaffold domains of the scaffolded fusion polypeptides of the invention display improved solubility in such aqueous solutions.

In their broadest sense, the scaffold strands are moieties that are capable of directing or limiting the conformations of the ends of the functional domain to which they are fused. As an illustrative cartoon example, the scaffold strands are polypeptides that are capable of interacting with one another so as to fix the ends of the functional domain in relatively close proximity to one another. Such polypeptides may comprise genetically encoded amino acid residues, non-genetically encoded amino acid residues, or derivatives or analogs thereof. Examples of such polypeptides include, by way of example and not limitation, polypeptides capable of coordinating, binding or chelating metals or metal ions, such as the zinc binding motifs or regions of zinc fingers; dimerizing peptide motifs; leucine zippers; helix-turn-helix motifs; coiled coils; homeodomains; and other polypeptide motifs known to those of skill in the art to be capable of limiting or directing the three-dimensional conformations of polypeptide to which they are fused. The scaffold strands are typically derived from the regions of such motifs that interact with one another. For example, the first scaffold strand may correspond to one helix of a helix-turn-helix motif, and the second strand may correspond to the other helix. As another example, each scaffold strand may correspond to a zinc binding region of a zinc finger such that the scaffold strands are capable of acting in concert to coordinate a zinc ion.

The scaffold strands may be linked to the functional domain via virtually any type of linkage known to those of skill in the art for linking moieties together. Typically, the linkage will be covalent, and may include an optional linker or spacer molecule. In embodiments in which the scaffolded fusion polypeptide will be expressed using biological systems, the scaffold strands are fused either directly to the N- and C-termini of the functional domain (one scaffold strand per terminus) or through a peptide linker. In embodiments in which the scaffolded fusion polypeptide is prepared synthetically or semisynthetically, the scaffold strands may be linked to the N- and C-termini of the functional domain using virtually any linkage chemistry that does not destroy the integrity of the scaffold and functional domains. The linkage may be mediated by way of a linker or spacer molecule, which may be biological or non-biological in nature.

A significant advantage of the scaffolded fusion polypeptides of the invention is that they are modular structures that can be linked together to form polymeric scaffolded fusion polypeptides. One module of such a polymeric scaffolded fusion polypeptide comprises a functional domain and a scaffold domain, as described above. A scaffolded fusion polypeptide can comprise a plurality of these modules ("polymeric scaffolded fusion polypeptides"), which permits the design and synthesis of forms of integral membrane proteins that span the membrane multiple times, such as, for example, soluble forms of cytokine receptors, G-protein coupled receptors (GCPR), ion channel receptors, and other integral membrane proteins known to those of skill in the art. These forms of the integral membrane proteins display significantly improved solubility. One exemplary polymeric scaffolded fusion polypeptide is a soluble form of the ECD of the CCR5 transmembrane receptor implicated in HIV infection.

In the polymeric forms of the scaffolded fusion polypeptides of the invention, the modules are linked together via their scaffold strands, either directly or with an optional linker or spacer. For example, the second scaffold strand of the first module may be linked to the first scaffold strand of the second module, and so forth. The functional domains of a polymeric scaffolded fusion protein can all correspond to regions of a single protein of interest, or they can correspond to regions from different proteins of interest. For example, the functional domain of the first module can correspond to a loop of the ECD of a first GPCR and the functional domain of the second module can correspond to a loop of the ECD of a second, different GPCR. As another example, the functional domains of a polymeric scaffolded fusion polypeptide can each correspond to soluble loops of two different transmembrane receptors that form a complex in the membrane. This modular format provides great flexibility regarding the types and complexities of the scaffolded fusion polypeptides that can be created.

The linkages linking the individual modules may be the same or different, and may themselves comprise a functional domain. As a consequence, forms of even complex integral membrane proteins that have improved solubility may be designed. For example, a scaffolded fusion polypeptide can be designed from the ECD or the ICD of an integral membrane protein. In one embodiment, the ends of a first loop of an ICD can each be fused to a pair of first and second scaffold strands to yield a first module. The other loops of the ICD can also be fused to pairs of first and second scaffold strands to yield further modules. The modules can be linked together to form a polymeric scaffolded fusion polypeptide corresponding to the ICD of the integral membrane protein. Similarly, a scaffolded fusion polypeptide can comprise the loops of an ECD.

In addition, a polymeric scaffolded fusion polypeptide corresponding to an entire integral membrane protein, including both the ICD and ECD, can be designed. For instance, each helix of the TMD of an integral membrane protein can be replaced by a scaffold strand to form the polymeric scaffold fusion polypeptide. In this embodiment, the functional domains of the polymeric scaffolded fusion polypeptide correspond to the loops of the ECD of the integral membrane protein, as described above, and the linkers linking the individual modules correspond to the loops of the ICD. Similarly, the functional domains of the polymeric scaffold fusion polypeptide can correspond to the loops of the ICD, and the linkers can correspond to the loops of the ECD.

In another aspect, the present invention provides nucleic acids for expressing the scaffolded fusion polypeptides of the invention. The nucleic acid may be an RNA or a DNA having a sequence that encodes the scaffolded fusion polypeptide operatively linked to a promoter sequence that directs or effects expression. In a particularly useful embodiment, the nucleic acid is a DNA expression vector. Such vectors generally comprise a promoter operatively linked to a polynucleotide that encodes the scaffolded fusion polypeptide.

In a particularly convenient embodiment, the coding sequence of such a vector may comprise one or more cassettes, each of which includes ends that correspond to restriction enzyme sites. Each cassette may encode an entire scaffolded fusion polypeptide, or alternatively, may encode one or more strands, domains or modules of a scaffolded fusion polypeptide. The ends corresponding to restriction enzyme sites can be used to insert or remove various domains or modules of the vector for the expression of a desired scaffolded fusion polypeptide.

In still another aspect, the present invention provides cells capable of expressing a scaffolded fusion polypeptide. The cells of the invention generally comprise a nucleic acid capable of expressing a scaffolded fusion polypeptide. The cells can be prokaryotic or eukaryotic, and the cells can be stably or transiently transfected with the nucleic acid.

In yet another aspect, the present invention provides methods of expressing a scaffolded fusion polypeptide. The methods comprise expressing a nucleic acid encoding a scaffolded fusion polypeptide of the invention and recovering the scaffolded fusion polypeptide. The expression can be carried out in cell-free as well as cell-based systems.

In a particularly convenient embodiment, host cells comprising a nucleic acid capable of expressing the scaffolded fusion polypeptide are cultured under conditions which permit expression and the expressed scaffolded fusion polypeptide is recovered from the culture.

The scaffolded fusion polypeptides of the invention will find use in virtually any type of method in which the integral membrane proteins from which they are designed find use. For example, the scaffolded fusion polypeptides are useful in a screening assay to identify compounds that bind the polypeptide, diagnostic methods and assays and, where applicable, as therapeutic agents. However, owing to their modular nature and improved solubility in membrane-free and detergent-free aqueous media, the scaffolded fusion polypeptides of the invention enable uses that are not achievable with the integral membrane protein from which they are designed.

For instance, the scaffolded fusion polypeptides of the invention can be used to generate antibodies that recognize the integral membrane proteins from which they were designed. In particular, a scaffolded fusion polypeptide corresponding to a specific loop of an ECD or an ICD of an integral membrane protein can be used to generate antibodies with specificity for that loop of the integral membrane protein. A polymeric scaffolded fusion polypeptide corresponding to loops or regions from different integral membrane proteins are particularly useful for generating antibodies that recognize a complex of the different integral membrane proteins. In addition, scaffolded fusion polypeptides can be used in screening assays to identify compounds that interact with loops or fragments of an ECD or an ICD. Furthermore, polymeric scaffolded fusion polypeptides can be used to competitively bind the ligand of a naturally occurring receptor in vitro or in vivo.

In addition, phage display systems and other display systems that display scaffolded fusion polypeptides can be used to display and/or screen soluble domains from proteins such as integral membrane proteins. Moreover, scaffolded fusion polypeptides, owing to their improved solubility compared to the proteins from which they were designed, can be used to probe the structure of the ECD or ICD, or both, of an integral membrane protein by techniques such as X-ray crystallography, nuclear magnetic resonance or circular dichroism. Scaffolded fusion polypeptides can even be used to rapidly assay the function of mutated portions of mutant integral membrane proteins without having to produce significant quantities of the entire mutant integral membrane protein. Thus, the scaffolded fusion polypeptides of the invention enable uses and methods that are unprecedented in the art.

In addition, the scaffolded fusion polypeptides can be used therapeutically. For example, scaffolded fusion polypeptides can be administered to modulate the activity of a receptor in vivo. Such scaffolded fusion polypeptides include those that are designed from the ECD of the receptor to competitively bind ligands of the receptor. In addition, such scaffolded fusion polypeptides include those designed to bind the receptor thereby inhibiting the function of the receptor. Examples include those that are designed from a soluble portion of a binding partner of the receptor. In a particularly useful embodiment, scaffolded fusion polypeptides that inhibit the activity of a receptor necessary for viral replication can be administered to treat or prevent an infection of the virus. For instance, a scaffolded fusion polypeptide designed from the ECD of the CCR5 transmembrane receptor can be administered to treat or prevent HIV infection.

4. BRIEF DESCRIPTION OF THE FIGURES

Figure 1A:
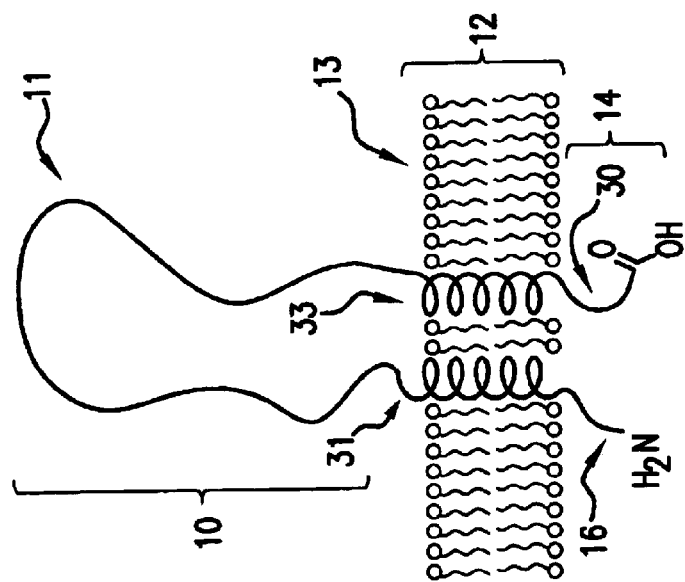

FIG. 1A provides a schematic representation of an exemplary integral membrane protein 2. This protein includes an extracellular domain (10), a transmembrane domain (12, shown embedded in cell membrane 13), and an intracellular domain (14). The extracellular domain is composed of an extracellular loop (11). The transmembrane domain is composed of two helical strands (31 and 33), each of which spans the membrane (13). The intracellular domain is composed of an N-terminal strand (16) and a C-terminal strand (30).

FIG. 1B provides a schematic representation of a scaffolded fusion polypeptide 4 of the invention designed from the integral membrane protein of FIG. 1A. Scaffolded fusion polypeptide 4 comprises an extracellular domain (ECD. 10'), a scaffold domain (15) and an intracellular domain (14'). The extracellular domain is composed of a functional domain (11') and the intracellular domain is composed of an N-terminal strand (16') and a C-terminal strand (30'). The scaffold domain is composed of a first scaffold strand (54) and a second scaffold strand (56). The scaffold domain also includes a zinc ion (50), which is coordinated with the first and second scaffold strands (54 and 56).

Figure 1C:
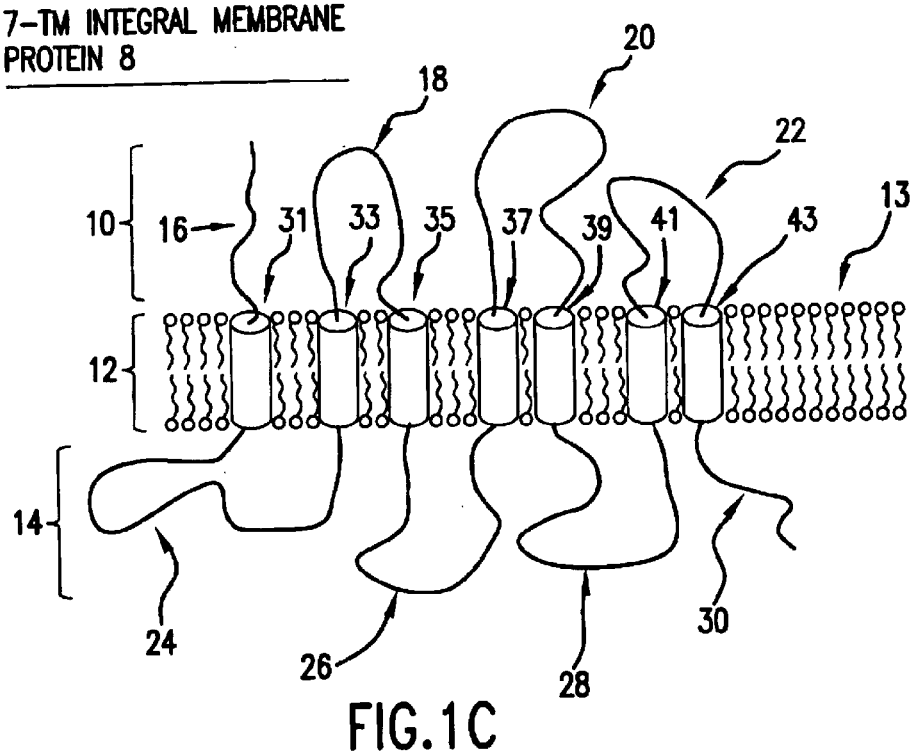

FIG. 1C provides a schematic representation of a typical 7-transmembrane protein 8. Transmembrane protein 8 comprises an extracellular domain (10), a transmembrane domain (12), and an intracellular domain (14). The extracellular domain comprises three loops (18, 20 and 22) and a terminal strand (16). The intracellular domain comprises three loops (24, 26 and 28) and a terminal strand (30). The transmembrane domain comprises seven strands (31, 33, 35, 37, 39, 41 and 43) that traverse the cell membrane (13).

Figure 1D:
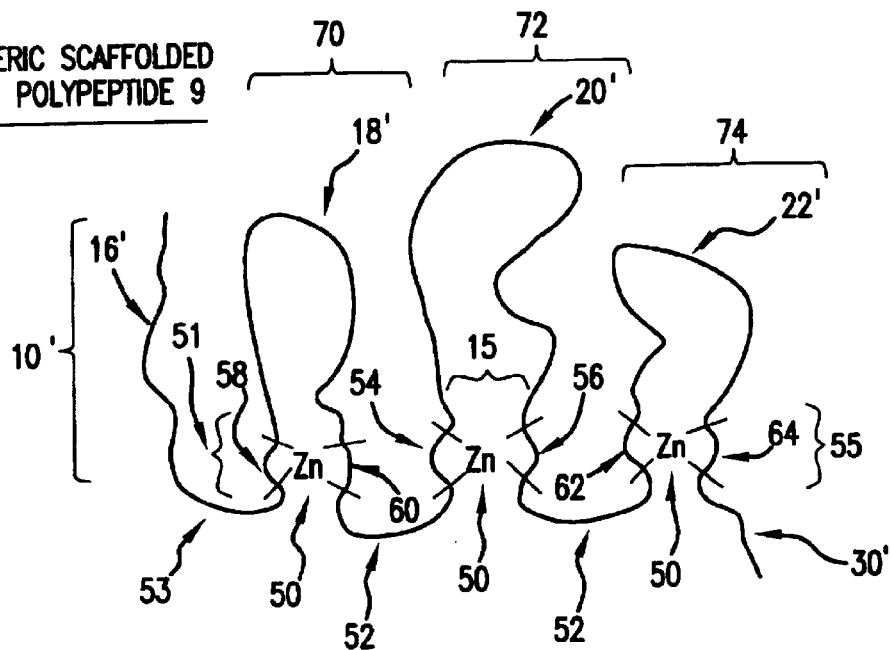

FIG. 1D provides a schematic representation of a scaffolded fusion polypeptide 9 designed from the extracellular domain of the 7-transmembrane protein of FIG. 1C. Polymeric scaffolded fusion polypeptide 9 comprises three modules (70, 72 and 74), each of which is conceptually similar to the scaffolded fusion polypeptide illustrated in FIG. 1B. Functional domain 18' and the first and second scaffold strands (58 and 60) together compose the first module (70). Functional domain 20' and the third and fourth scaffold strands (54 and 56) together compose the second module (72). Functional domain 22' and the fifth and sixth scaffold strands (62 and 64) together compose the third module (74). Extracellular domain (ECD) 10' (or, alternatively intracellular domain, ICD) of polymeric scaffolded fusion polypeptide 9 comprises three functional domains (18', 20' and 22') and a terminal strand (16'). Functional domains 18', 20' and 22' are each held in place by a scaffold domain (51, 15 and 55, respectively) which includes a zinc ion (50). Modules 70, 72 and 74 are linked serially together via linkers (52). Terminal strand 16', is linked to module 70 via a linker (53). Polymeric scaffolded fusion polypeptide 9 additionally includes terminal strand 30'.

FIG. 1E provides a schematic representation of artificial receptor according to the present invention. Artificial receptor 8' is similar to the scaffolded fusion polypeptide 9 of FIG. 1D except that linkers 52 and 53 of the scaffolded fusion polypeptide 9 correspond to functional domains 24', 26' and 28' of the artificial receptor 8' of FIG 1E.

Figure 2:
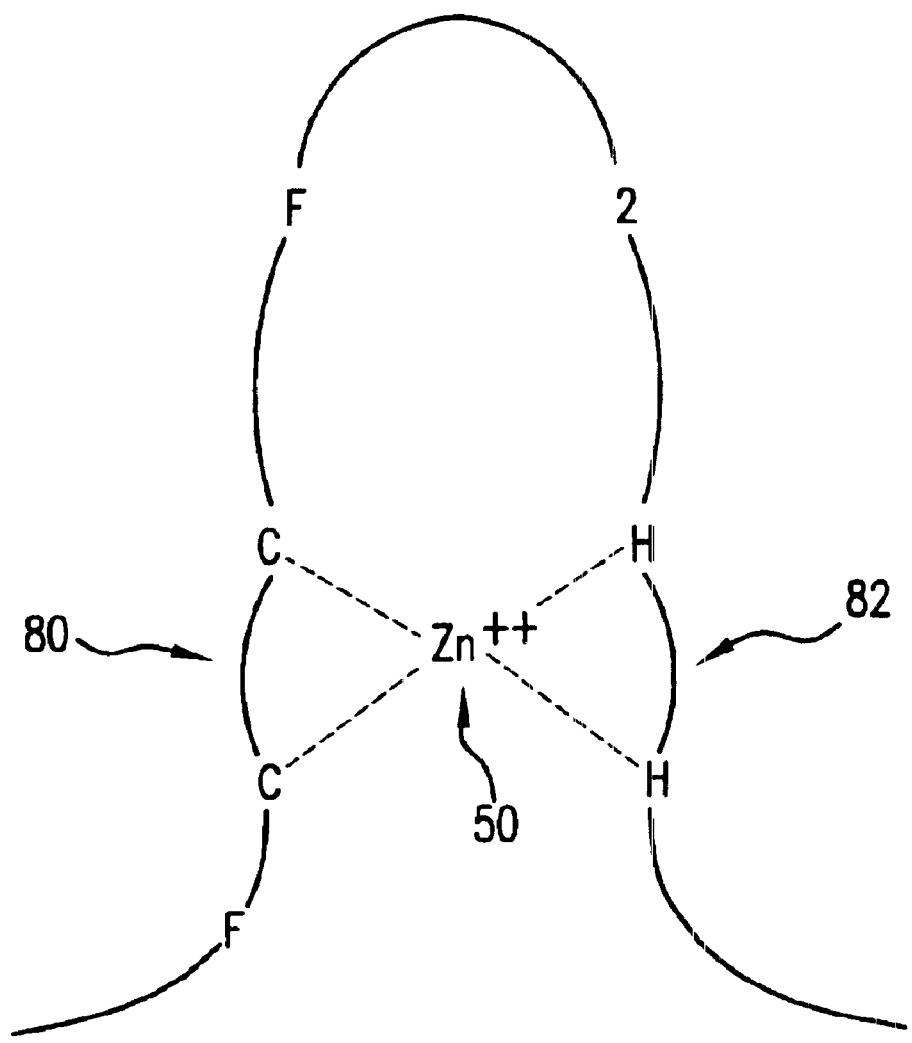

FIG. 2 provides a schematic representation of a typical zinc finger polypeptide motif. A zinc finger domain comprises two strands (80 and 82) that together chelate a zinc ion (50). Strand 80 includes two cystidine (C) residues that coordinate the zinc ion, and strand 82 comprises two histidine (H) residues that also coordinate the zinc ion.

5. DETAILED DESCRIPTION OF THE PREFERRED EMBODIMENTS

As discussed in the Background section, to date there are no known generally applicable methods which permit the isolation, synthesis or expression of integral membrane proteins, or domains of interest thereof, that provide high yield while retaining relevant structure and activity.

The present invention addresses these and other shortcomings in the art by providing novel compositions designed from integral membrane proteins and that mimic or possess one or more of the biological activities of integral membrane proteins from which they were designed. Moreover, in many instances compositions will exhibit improved solubility in cell-free and detergent-free aqueous media compared to the integral membrane protein from which they were designed.

5.1 Abbreviations

The amino acid notations used herein for the twenty genetically encoded L-amino acids are conventional and are as follows:

| Amino Acid | One-Letter Abbreviation | Three Letter Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

As used herein, unless specifically delineated otherwise, the three-letter amino acid abbreviations designate amino acids in the L-configuration. Amino acids in the D-configuration are preceded with a "D-." For example, Arg designates L-arginine and D-Arg designates D-arginine. Likewise, the capital one-letter abbreviations refer to amino acids in the L-configuration. Lower-case one-letter abbreviations designate amino acids in the D-configuration. For example, "R" designates L-arginine and "r" designates D-arginine.

Unless noted otherwise, when polypeptide sequences are presented as a series of one-letter and/or three-letter abbreviations, the sequences are presented in the N->C direction, in accordance with common practice.

The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (U). Also, unless specified otherwise, nucleic acid sequences that are represented as a series of one-letter abbreviations are presented in the 5'→3' direction.

5.2 Definitions

As used herein, the following terms shall have the following meanings:

"Genetically Encoded Amino Acid" refers to L-isomers of the twenty amino acids that are defined by genetic codons. The genetically encoded amino acids are the L-isomers of glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine and lysine.

"Genetically Non-Encoded Amino Acid" refers to amino acids that are not defined by genetic codons. Genetically non-encoded amino acids include derivatives or analogs of the genetically-encoded amino acids that are capable of being enzymatically incorporated into nascent polypeptides using conventional expression systems, such as selenomethionine (SeMet) and selenocysteine (SeCys); isomers of the genetically-encoded amino acids that are not capable of being enzymatically incorporated into nascent polypeptides using conventional expression systems, such as D-isomers of the genetically-encoded amino acids; L- and D-isomers of naturally occurring α-amino acids that are not defined by genetic codons, such as α-aminoisobutyric acid (Aib); L- and D-isomers of synthetic α-amino acids that are not defined by genetic codons; and other amino acids such as β-amino acids, γ-amino acids, etc. In addition to the D-isomers of the genetically-encoded amino acids, exemplary common genetically non-encoded amino acids include, but are not limited to, norleucine (Nle), penicillamine (Pen), N-methylvaline (MeVal), homocysteine (hCys), homoserine (hSer), 2,3-diaminobutyric acid (Dab) and ornithine (Orn). Additional exemplary genetically non-encoded amino acids are found, for example, in *Practical Handbook of Biochemistry and Molecular Biology*, 1989, Fasman, Ed., CRC Press, Inc., Boca Raton, Fla., pp. 3–76 and the various references cited therein.

"Extracellular Domain" or "ECD" refers collectively to all loops or strands of an integral membrane protein that reside on the exterior (extracellular) side of the cell. For example, the ECD of the integral membrane protein illustrated in FIG. 1A comprises loop 10. As another example, the ECD of the 7-transmembrane integral membrane protein illustrated in FIG. 1C comprises loops 18, 20 and 22 and terminal strand 16.

"Intracellular Domain" or "ICD" refers collectively to all loops or strands of an integral membrane protein that reside on the interior (intracellular) side of the cell. For example, the ICD of the integral membrane protein illustrated in FIG. 1A comprises terminal strands 16 and 30. As another example, the ICD of the 7-transmembrane integral membrane protein illustrated in FIG. 1C comprises loops 24, 26 and 28 and terminal strand 30.

"Transmembrane Domain" or "TMD" refers collectively to all strands of an integral membrane protein that traverse the cell membrane. For example, the TMD of the integral membrane protein illustrated in FIG. 1A comprises strands 31 and 33 (illustrated as helical in FIG. 1A). The TMD of the 7-transmembrane integral membrane protein illustrated in FIG. 1C comprises strands 31, 33, 35, 37, 39, 41 and 43 (illustrated as cylinders in FIG. 1C).

"TMD Helix" refers to an individual strand of an integral membrane protein, whether helical or non-helical in structure, that traverses the cell membrane. For example, strands 31 and 33 of the integral membrane protein illustrated in FIG. 1A are each TMD helices. Likewise, strands 31, 33, 35, 37, 39, 41 and 43 of the 7-transmembrane integral membrane protein illustrated in FIG. 1C are each TMD helices.

"Function" or "Activity" refers to a biological activity of a molecule of the invention. The biological activity is any activity recognized by those of skill in the art. For instance, biological activities include ligand binding, antibody binding, receptor signaling, other intermolecular interactions, immunogenicity and other biological activities recognized by those of skill in the art. In particular, when a scaffolded fusion polypeptide retains or mimics the function or activity of an integral membrane protein, the scaffolded fusion polypeptide should mimic or retain at least one biological activity of the integral membrane protein.

5.3 Scaffolded Fusion Polypeptides

The scaffolded fusion polypeptides of the invention may be designed from any integral membrane protein that has a soluble domain, such as an extracellular domain (ECD) or an intracellular domain (ICD) of a cell surface receptor, and a transmembranic domain (TMD) that anchors the protein within the membrane lipid bilayer. In addition, scaffolded fusion polypeptides can be designed from the soluble domains of other transmembrane proteins like nuclear membrane proteins, mitochondrial membrane proteins, endoplasmic reticulum membrane proteins and other integral membrane proteins known to those of skill in the art to have soluble domains. Most useful are those integral membrane proteins in which the TMD comprises two or more TMD helices that each span the membrane (see, e.g., the integral membrane protein illustrated in FIG. 1A). Examples of such integral membrane proteins include, by way of example and not limitation, cytokine receptors, serpentine receptors, G-protein coupled receptors ("GPCRs"), ion-channel receptors, opiod receptors, cell surface receptors found on immune cells (e.g., CDR4 and CCR5) and cell adhesion proteins.

In the scaffolded fusion polypeptides of the invention, which may be designed from the entire integral membrane protein or from one or more domains or loops thereof (as will be described in more detail below), the transmembrane domain is replaced with a soluble scaffold domain, such that the resultant scaffolded fusion polypeptide displays improved solubility in membrane-free and detergent-free aqueous solution while retaining one or more of the biological activities of the integral membrane protein, or domain(s) or loops thereof, from which it was designed.

Referring to FIG. 1A, a typical cell-surface integral membrane protein 2 from which a scaffolded fusion polypeptide may be designed includes an ECD 10, a TMD 12 (shown embedded in membrane 13) and an ICD 14. Although the illustrative example is n cell surface integral membrane protein, scaffolded fusion polypeptides may also be designed from other integral membrane proteins with soluble domains such as integral membrane proteins of nuclear membranes, mitochondrial membranes, endoplasmic reticulum membranes and other intracellular membranes. In such integral membrane proteins, those of skill in the art will recognize one or more soluble domains that correspond to ECD 10 and/or ICD 14. As illustrated in FIG. 1A, the ECD is composed of loop 11. The TMD 12 is composed of two helical strands 31, 33, each of which spans membrane 13. The ICD is composed of N-terminal strand 16 and C-terminal strand 30. Any of the illustrated loops, helices and strands may have, but need not have biological activity. In many integral membrane proteins, the ECD 10 often functions to bind ligands.

Referring to FIG. 1B, a scaffolded fusion polypeptide of the invention 4 may be designed from integral membrane protein 2. Scaffolded fusion polypeptide 4 comprises a an ECD 10', a scaffold domain 15 and an ICD 14'. Similar to the integral membrane protein 2 from which scaffolded fusion polypeptide 4 was designed, ECD 10' is composed of functional domain 11' and ICD 14' is composed of N-terminal strand 16' and C-terminal strand 30'. Scaffold domain 15 is composed of a first scaffold strand 54 and a second scaffold strand 56. In the specific embodiment illustrated in FIG. 1B, scaffold domain 15 also includes a zinc ion 50, which is coordinated with the first and second scaffold strands 54, 56. Unlike integral membrane protein 2, scaffolded fusion polypeptide 4 is not shown embedded within a membrane (13), as scaffolded fusion polypeptide 4 displays improved solubility in membrane-free and detergent-free aqueous environments and retains one or more activities of integral membrane protein 2.

5.3.1 The ECD and Functional Domain

Functional domain 11' corresponds to loop 11 of integral membrane protein 2. As will be recognized by those of skill in the art, while the illustrated integral membrane protein 2 has an ECD 10 which comprises a single loop 11, functional domain 11' may correspond to any intracellular or extracellular loop or strand of an integral membrane protein, such as a loop of an ECD or an ICD of a GPCR or other receptor in which the ECD and/or ICD comprises multiple loops. Examples of scaffolded fusion polypeptides in which the ECD comprises several functional domains are described in a later section. The amino acid sequence of functional domain 11' may correspond identically to the amino acid sequence of loop 10 of integral membrane protein 2. Alternatively, it may include one or more mutations, which may be conservative or non-conservative or consist of insertions or deletions, as are well-known in the art. Preferably, such mutated functional domains 11' will retain at least some biological activity. Alternatively, scaffolded fusion polypeptides of the invention including mutated functional domains 11' of unknown activity may be designed and synthesized as a convenient means of assessing the affect of such mutations on the activity of the functional domain, and by correlation upon the loop of the integral membrane protein 2 to which functional domain 11' corresponds. Preferably, the amino acid sequence of functional domain 11' will correspond identically to the sequence of loop 11.

The starting and ending points (i.e., the N- and C-termini) of functional domain 11' may align identically with the starting and ending points of loop 11, or they may, independently of one another, include one or a few additional amino acids corresponding to the amino acid residues of their respective adjacent TMD helices. If such additional residues are included, their number should be sufficiently few so as to avoid significantly increasing the hydrophobicity of scaffolded fusion polypeptide 4, as this may deleteriously affect the solubility of the polypeptide. Preferably, no more than 1 or 2 such additional amino acids are included.

Alternatively, one or both of the ending points, independently of one another, may be truncated by one or more amino acid residues. Care should be taken to insure that a sufficient number of amino acids remain such that functional domain 11' retains the desired biological activity(ies).

Where the starting and ending points of loop 11 are unknown, they can be readily ascertained from the sequence of integral membrane protein 2 in conjunction with hydropathy analyses or plots (see, e.g., Kyte & Doolittle, 1982, J. Mol. Biol. 157:105–132), as well as other methods, such as sequence alignments, as are known in the art.

5.3.2 The ICD

The ICD of scaffolded fusion polypeptide 4 is composed of N-terminal strand 16' and C-terminal strand 30'. N- and C-terminal strands 16' and 30' may each, independently of one another, correspond identically to the respective N- and C-terminal strand of integral membrane protein 2. Alternatively, they may be mutated, as previously described for functional domain 11', or they may be completely artificial in sequence or even absent altogether. Conveniently, either N-terminal strand 16' or C-terminal strand 30' can comprise a protein purification tag, such as a polyhistidine tag, to facilitate isolation of the scaffolded fusion polypeptide.

5.3.3 The Scaffold Strands and Domain

Scaffold strands 54 and 56, together with any metal or metal ion coordinated or bound thereto (in FIG. 1B illustrated as zinc ion 50), constitute scaffold domain 15. As illustrated by comparing integral membrane protein 2 with scaffolded fusion polypeptide 4, scaffold domain 15 corresponds to TMD 12, and serves to supply the structural framework to the ends of functional domain 11' that are provided to loop 11 by TMD 12 of integral membrane protein 2. Thus, scaffold domain 15 "mimics" the structural contributions of TMD 12 without mimicking the hydrophobic properties of TMD 12. Thus, replacing TMD 12 with scaffold domain 15 permits the design and synthesis of a polypeptide (the scaffolded fusion polypeptide 4) that retains one or more biological activities of the integral membrane protein from which it was designed and at the same time displays improved solubility in a membrane-free and detergent-free aqueous medium. In addition, scaffold domain 15 also provides a framework for functional domain 11' that corresponds to the contribution of TMD 12 to the structure of loop 11 in integral membrane protein 2.

A scaffold strand can be any structure capable of interacting with another structure so as to structurally constrain in proximity to one another the ends of a polypeptide to which the structures are fused. A scaffold strand should be capable of forming linkages to either end of the functional domain. Preferably, a scaffold strand should be also capable of forming additional linkages for the creation of polymeric forms of the scaffolded fusion polypeptides that are capable of mimicking the activity of complex receptors such as GPCRs (discussed in more detail in a later section).

Preferred scaffold strands are derived from polypeptide motifs that exhibit the above-described characteristics. For instance, preferred scaffold strands are derived from proteins or peptides comprising metal chelating motifs, polyhistidine motifs, nucleic acid binding motifs, zinc finger motifs, helix-turn-helix motifs, homeodomains, leucine zippers, coiled coils, cystine disulfide bridges and other motifs known to those of skill in the art to be capable of serving as scaffold strands. Preferred scaffold strands are also derived from dimerizing peptide motifs known to those of skill in the art such as those described in Bodenmuller et al., 1986, *EMBO J.* 5: 1825–1829 and in Xu et al., 2001, *Nature Genet.* 27:23–29.

Each scaffold strand of the scaffold domain will typically correspond, preferably identically, to a portion of the selected polypeptide motif from which the scaffold domain corresponds. For example, a peptide with the sequence EFLIVIK is known to form dimers with other peptides with the same or similar sequences (Xu et al., 2001, supra). If the scaffold domain is designed from a pair of dimerizing peptide motifs, each peptide having the sequence EFLIVIKS (SEQ ID NO:1)(Xu et al., 2001, supra), each scaffold strand will typically have a sequence corresponding to an EFLIVIKS (SEQ ID NO:1). Dimerization of the scaffold strands provides an effective scaffold domain.

A preferred scaffold domain is a metal chelating motif derived from a naturally occurring zinc finger protein. The metal chelating motif of a zinc finger protein generally fits the $Cys_2His_2$ consensus with an amino acid sequence corresponding to (Phe,Tyr)-Xaa-Cys-$X_{2-4}$-Cys-Xaa$_3$-Phe-Xaa$_5$-Leu-Xaa$_2$-His-Xaa$_{3-5}$-His (SEQ ID NO:2). For example, a consensus metal chelating motif from an alignment of 131 zinc finger proteins has the sequence Cys-Pro-Glu-Cys-Xaa$_n$-His-Gln-Arg-Thr-His (SEQ ID NO:3) wherein the two Cys and two His residues are capable of coordinating a zinc ion and wherein Xaa$_n$ represents a loop of 'n' residues which varies in length and amino acid sequence among the 131 zinc finger proteins. See Desjarlais and Berg, 1993, *Proc. Natl. Acad. Sci. USA* 90:2256–2260. Typically, referring to FIG. 2, a zinc finger domain comprises two strands 80 and 82 that together chelate a zinc ion 50. Strand 80 includes two Cys residues that coordinate zinc ion 50, and strand 82 comprises two His residues that also coordinate zinc ion 50.

While not intending to be bound by any particular theory, it is believed that the two Cys residues and the two His residues of the motif are capable of chelating a zinc ion under the appropriate conditions. For the purposes of the present invention, a scaffold strand can correspond to a portion of the $Cys_2His_2$ consensus, e.g. strand 80. A complementing scaffold strand can correspond to a complementary portion of the $Cys_2His_2$ consensus, e.g. strand 82. However, the particular sequence of the scaffold strand is not crucial so long as the scaffold strand can bind a metal ion or form a stable secondary or tertiary structure. As a specific example, one or both of the His residues of the $Cys_2His_2$ consensus can be replaced with a Cys residue. As another example, one or both of the Cys residues can be replaced with a His residue. Preferably, a scaffold strand comprises two Cys residues, two His residues, or one Cys residue and one His residue.

As illustrated in FIG. 1B, each scaffold strand 54, 56 of scaffold domain 15 is fused to an end of functional domain 11'. In a scaffold domain derived from a zinc finger motif, scaffold strand 54 can correspond to, for instance, one of the metal binding strands of a zinc finger motif such as strand 80, for example, with the sequence (Phe,Tyr)-X-Cys-$X_{2-4}$-Cys (SEQ ID NO:4). Similarly, complementary scaffold strand 56 can correspond to the complementary metal binding strand 82 of a zinc finger motif, for example, with the sequence His-$X_{3-5}$-His (SEQ ID NO:5), thereby complementing strand 54.

In one embodiment of the invention, in a preferred scaffold domain the first scaffold strand has the amino acid sequence Tyr-Lys-Cys-Gly-Leu-Cys (SEQ ID NO:6) and the second scaffold strand has the amino acid sequence His-Gln-Arg-Val-His (SEQ ID NO:7). The amino terminus of a functional domain is linked to the carboxy terminus of SEQ ID NO:6, and the carboxy terminus of the functional domain is linked to the amino terminus of SEQ ID NO:7, or vice versa. The linkage may be direct, or mediated via a spacer, as described below.

In a polymeric scaffolded fusion polypeptide, discussed below, the amino terminus of SEQ ID NO:6 or the carboxy terminus of SEQ ID NO:7, or both, are linked to the remainder of the polymeric scaffolded fusion polypeptide.

5.4 Spacers

The scaffold strands and the functional domains can be linked together either directly or via an optional spacer. The spacers of a scaffolded fusion polypeptide can be any moieties known to those of skill in the art to be capable of linking one moiety to a second moiety. The spacer may be rigid, semi-rigid or flexible, hydrophilic or hydrophobic, long or short, etc. A plethora of spacers suitable for linking strands or domains are known in the art. The actual choice of spacer will depend upon, among other things, the nature of the scaffolded fusion polypeptide, the length vs. rigidity of the spacer, etc., and will be apparent to those of skill in the art. Preferred spacers are peptides or polypeptides that do not interfere with the function of the scaffold strand, the functional domain or the scaffolded fusion polypeptide.

5.5 Scaffolded Fusion Polypeptides Designed from Other Proteins

In another embodiment of the invention, scaffolded fusion polypeptides may be designed from other proteins, including peripheral membrane proteins, soluble proteins and other proteins, using the principles discussed above. In particular, a loop, region or other domain of any protein may used to design a scaffolded fusion polypeptide. Scaffolded fusion polypeptides can be designed from, for instance, loops of the antigen combining regions of immunoglobulins, ligand binding domains of soluble receptors, nucleic acid binding domains of nucleic acid binding proteins and other domains of these proteins and other proteins known to those of skill in the art.

Preferred domains for the design of scaffolded fusion polypeptides are soluble domains. For instance, in a protein that comprises a hydrophobic core and soluble surface domains, a soluble surface domain is preferred for the design of scaffolded fusion polypeptides. In a scaffolded fusion polypeptide 4 of this embodiment of the invention, functional domain 11' corresponds to the domain of the protein selected for the design of the scaffolded fusion polypeptide. Scaffold domain 15 of the scaffolded fusion polypeptide can be used to hold together the ends of the domain of the selected protein thereby constraining the overall conformation of the domain.

5.6 Polymeric Scaffolded Fusion Polypeptides

In still another embodiment of the invention, scaffolded fusion polypeptide modules can be linked together to form a polymeric scaffolded fusion protein. A scaffold fusion polypeptide module comprises a functional domain fused to a scaffold domain, as described above (see, e.g., FIG. 1B). Scaffolded fusion polypeptide modules can conveniently be linked together to incorporate multiple functional domains into a polymeric scaffolded fusion polypeptide. Polymeric scaffolded fusion polypeptides are particularly useful for designing molecules that mimic complex soluble portions of integral membrane proteins, such as an ECD or ICD with multiple loops, and that exhibit improved solubility in a membrane-free and detergent-free aqueous medium.

For example, a polymeric scaffolded fusion polypeptide can correspond to an entire ECD or ICD of a naturally occurring integral membrane protein. A representative example of the design of such a fusion polypeptide is illustrated in FIGS. 1C and 1D.

Referring to FIG. 1C, 7-transmembrane integral membrane protein ("7TM protein") 8 comprises an ECD 10, a TMD 12 (illustrated embedded in membrane 13) and an ICD 14. Those of skill in the art will recognize that the ICD and ECD could be reversed. For example, the ECD could be 14 and the ICD could be 10. ECD 10 is composed of loops 18, 20 and 22 and terminal strand 16, which can be either an N-terminal or C-terminal strand. TMD 12 is composed of seven helices—TMD helices 31, 33, 35, 37, 39, 41 and 43 (illustrated as cylinders). ICD 14 is composed of loops 24, 26 and 28 and terminal strand 30, which can be either a C-terminal strand or an N-terminal strand, depending upon the polarity of terminal strand 16.

FIG. 1D illustrates an exemplary polymeric scaffolded fusion polypeptide 9 designed from 7TM protein 8 of FIG. 1C. Polymeric scaffolded fusion polypeptide 9 comprises three modules 70, 72 and 74, each of which is conceptually similar to the scaffolded fusion polypeptide illustrated in FIG. 1B. ECD 10' (or, alternatively ICD) of polymeric scaffolded fusion polypeptide 9 comprises functional domains 18', 20' and 22' and terminal strand 16', which correspond to loops 18, 20 and 22 and terminal strand 16 of 7TM protein 8, in a manner as previously described for integral membrane protein 2 and scaffolded fusion polypeptide 4 (FIGS. 1A & 1B). Functional domains 18', 20' and 22' are each held in place by a scaffold domain-illustrated as scaffold domains 51, 15 and 55, respectively.

Modules 70, 72 and 74 are linked serially together via linkers 52, which are illustrated in the exemplary embodiment as being the same, but may be different. As illustrated, terminal strand 16', which corresponds to terminal strand 16 of 7TM protein 8 (either identically or non-identically, as previously described) is linked to module 70 via linker 53, which may be the same or different as the linkers 52 linking modules 70, 72 and 74. Alternatively, terminal strand 16' may be fused directly to first scaffold strand 58 of scaffold module 51 without the aid of linker 53. In a particularly convenient embodiment of the invention, one or more linkers of a polymeric scaffolded fusion polypeptide comprise an affinity tag, such as a polyhistidine tag, to facilitate affinity purification of the polymeric scaffolded fusion polypeptide.

Lastly, as illustrated, polymeric scaffolded fusion polypeptide 9 includes terminal strand 30', which corresponds to terminal strand 30 of 7TM protein 8. Terminal strand 30' may correspond identically to terminal strand 30 of 7TM protein 8, or it may contain mutations, as previously described. Alternatively, it may be completely artificial in sequence or even absent altogether. Conveniently, terminal strand 30' can also comprise an affinity tag, such as a polyhistidine tag, for affinity purification of polymeric scaffolded fusion polypeptide 9.

5.6.1 Linkers

In a polymeric scaffolded fusion polypeptide, the scaffold strands can be linked together either directly or via an optional linker. The linkers of a polymeric scaffolded fusion polypeptide can be any moieties known to those of skill in the art to be capable of linking one moiety to a second moiety. In particular, a linker may be any of the spacers discussed above. One suitable linker for scaffold domains derived from zinc finger motifs is the Kruppel-type linker peptide with the sequence Thr-Gly-Glu-Lys-Pro-Tyr-Lys (SEQ ID NO:8) (Liu et al., 1997, *Proc Natl. Acad. Sci. USA* 94:5525–5530).

In a preferred embodiment, a linker is a peptide or a polypeptide that has biological function. For instance, when a scaffolded fusion polypeptide corresponds to an ECD of an integral membrane protein, the linkers can correspond to, for instance, the ICD of the integral membrane protein, or vice versa. As such, the scaffolded fusion protein can comprise all of the soluble functional domains of the integral membrane protein, with a scaffold of scaffold domains replacing the TMD of the integral membrane protein.

For example, one such embodiment of an artificial receptor 8' is illustrated in FIG. 1E, which is identical to FIG. 1D except that linkers 52 and 53 correspond to ICD loops 24, 26 and 28 (illustrated in FIG. 1E as functional domains 24', 26' and 28') of 7-TM protein 8 (FIG. 1C). In addition, the linkers can have any other biological function known to those of skill in the art.

5.6.2 Scaffolded Fusion Polypeptide Corresponding to the ECD of CCR5:

In a specific embodiment, the present invention provides a scaffolded fusion polypeptide that corresponds to the ECD of the 7TM protein CCR5 with improved solublity. The 7TM CCR5 is a cofactor for the entry of certain strains of human and simian immunodeficiency viruses. Signoret et al., 2000, *J Cell Biol* 151:1281–94. CCR5 is a 7-helix transmembrane protein from the family of G-protein coupled receptors ("GPCRs"). Efremov et al., 1999, *Eur J Biochem* 263:746–56. Since CCR5 has been implicated in HIV infection, scaffolded fusion polypeptides can be used to treat or prevent HIV infection in mammals including humans. Such scaffolded fusion polypeptides include those that correspond to the ECD of CCR5 which can bind the portions of HIV that interact with the ECD of CCR5 thereby preventing association of HIV with CCR5.

CCR5 possesses an ECD, an ICD and a TMD component of seven transmembrane helices. The ECD of CCR5 comprises an amino terminal strand and three loops. For the following discussion, the three loops of the ECD of CCR5 are referred to as loops 1–3. The amino acid sequence of CCR5 (SEQ ID NO:9) is presented, for example, at GenBank accession no. XM_002925.1 and at GenBank accession no. XP_002925.1, the contents of which are hereby incorporated by reference in their entirety.

The sequence of the CCR5 scaffolded fusion polypeptide is presented in Table 2 below. In Table 2, the various segments of the CCR5 scaffolded fusion polypeptide are separated by spaces for convenience. The spaces do not indicate gaps in the sequence of the CCR5 scaffolded fusion polypeptide.

In the scaffolded CCR5 fusion polypeptide, first module 70 is linked to second module 72 via a six amino acid peptide linker 52, with the amino acid sequence GHHHHS (SEQ ID NO:15) as shown in Table 2, and second module 72 is linked to third module 74 via a five amino acid peptide linker 52 with the amino acid sequence GGGGS (SEQ ID NO:16). The polyhistidine motif of SEQ ID NO:15 may be conveniently used as an affinity tag to isolate and purify the CCR5 scaffolded fusion polypeptide.

The CCR5 scaffolded fusion polypeptide of the present invention mimics the function of all or a portion of the 7TM CCR5. As shown in the Examples below, a CCR5 scaffolded fusion polypeptide is specifically bound by antibodies specific for the native CCR5. In addition, the CCR5 scaffolded fusion polypeptide of the present invention can be used to generate antibodies, according to techniques known to those of skill in the art, that recognize the naturally occurring CCR5 receptor in its native environment. In addition, the

TABLE 2

Amino Acid Sequence of CCR5 Scaffolded Fusion Polypeptide

MDYQVSSPIYDINYYTSEPCQKINVKQIAA YKCGL AAAQWDFGNTMCQ HQRVH   (SEQ ID NO:10)

GHHHHS YKCGLC TRSQKEGLHYTCSSHFPYSQYQFWKNFQTLKI HQRVH GGGGS

YKCGLC QEFFGLNNCSSSNRLDG HQRVH AA

With reference to FIG. 1D, in the scaffolded CCR5 fusion polypeptide of the present invention (SEQ ID NO:10), the amino terminal strand 16' corresponds identically to the amino terminal strand of CCR5, residues 1–30 having the sequence MDYQVSSPIYDINYYTSEPCQKINVKQIAA (SEQ ID NO:11). This strand is fused directly to the amino terminus of a first scaffold strand 58 which has the sequence YKCGLC (SEQ ID NO:6), without the aid of a linker. The amino terminal strand of functional domain 18' which corresponds identically to loop 1 of CCR5, residues 90–102 having the amino acid sequence AAAQWDFGNTMCQ (SEQ ID NO:12), is fused to the carboxy terminus of the first scaffold strand 58, and the the amino terminus of the second scaffold strand 60. The second scaffold strand 60 has the amino acid sequence HQRVH (SEQ ID NO:7). Functional domain 18' and the first and second scaffold strands 58, 60 together compose the first module 70 of the CCR5 scaffolded fusion polypeptide.

Similarly, functional domain 20', which corresponds identically to loop 2 of CCR5, residues 167–198 having the amino acid sequence TRSQKEGLHYTCSSHFPYSQYQFWKNFQTLKI (SEQ ID NO:13) is fused to third and fourth scaffold strands 54, 56. In the CCR5 scaffolded polypeptide, the third and fourth scaffold strands share the same sequences as the first and second scaffold strands, respectively, i.e. SEQ ID NO:6 and SEQ ID NO:7. Functional domain 20' and the third and fourth scaffold strands 54, 56 together compose the second module 72 of the CCR5 scaffolded fusion polypeptide.

Finally, functional domain 22', which corresponds identically to loop 3 of CCR5, residues 261–277 having the amino acid sequence QEFFGLNNCSSSNRLDG (SEQ ID NO:14), is fused to a fifth scaffold strand 62 with the amino acid sequence of SEQ ID NO:6 and a sixth scaffold strand 64 with the amino acid sequence of SEQ ID NO:7. Functional domain 22' and the fifth and sixth scaffold strands 62, 64 together compose the third module of the CCR5 scaffolded fusion polypeptide.

CCR5 scaffolded fusion polypeptide can be used to screen for molecules that interact with the naturally occurring CCR5 receptor such as CCR5 agonists and CCR5 antagonists. However, quite unlike the native 7TM CCR5, the CCR5 scaffolded fusion polypeptide of the invention displays improved solubility in membrane-free and detergent-free aqueous medium. Thus, the CCR5 scaffolded fusion polypeptide of the invention enables cell-free uses and assays that are not achievable with the native 7TM CCR5 protein.

5.7 Nucleic Acids for Expressing Scaffolded Fusion Polypeptides

In another aspect, the present invention provides nucleic acids that can be used for the expression of the scaffolded fusion polypeptides of the invention. In particular, the present invention provides nucleic acids that are capable of expressing any of the scaffolded fusion polypeptides discussed above. For example, one nucleic acid of the present invention is capable of expressing the CCR5 scaffolded fusion polypeptide (SEQ ID NO:10).

The nucleic acid can be an RNA or a DNA and may be double stranded or single stranded. Typically, the nucleic acids of the present invention comprise a double stranded DNA or a single stranded RNA sequence that encodes a scaffolded fusion polypeptide operably linked to a promoter sequence that is capable of directing or effecting the expression of the scaffolded fusion polypeptide.

In a particularly convenient embodiment of the invention, the sequence encoding a scaffolded fusion polypeptide can comprise one or more cassettes which encodes a scaffolded fusion polypeptide or a module, domain or strand thereof. Each cassette typically comprises a sequence that encodes a scaffolded fusion polypeptide or any module, domain or strand thereof and, in addition, comprises convenient ends that correspond to restriction enzyme sites. The ends of the cassettes enable one of skill in the art to design a nucleic acid of the invention by mixing and matching various cassettes that encode modules, domains or strands by techniques well known to those of skill in the art to facilely create a wide variety of different scaffolded fusion polypeptides of interest. For instance, if the cassettes have ends corresponding to the appropriate restriction enzyme sites, a cassette encoding a first scaffold strand can be linked to a cassette encoding a functional domain which can, in turn, be linked to a cassette encoding a second scaffold strand to create a new cassette that encodes a monomeric scaffolded fusion protein or a single module of a polymeric scaffolded fusion protein. Furthermore, multiple cassettes encoding such modules can be linked together to create a nucleic acid that encodes a polymeric scaffolded fusion protein. In nucleic acids of the invention that comprise cassettes, cassettes can conveniently be replaced, for instance, to substitute a module, domain or strand of a scaffolded fusion protein encoded by the nucleic acid. Since the ends of the cassettes might encode amino acids of the scaffolded fusion polypeptide, care should be taken in the selection of the restriction enzyme sites to which the ends correspond so that the encoded amino acids do not interfere with the function of the encoded scaffolded fusion polypeptide. Alternatively, the restriction sites can be removed by standard site directed mutagenesis techniques.

The promoter sequence of the nucleic acid should be selected based upon the expression system. For instance, a particularly useful nucleic acid is a DNA expression vector that is capable of encoding a scaffolded fusion polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions. A particularly convenient vector is a cassette vector which comprises expression cassettes, as previously described.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides encoded by nucleic acids as described herein.

The recombinant expression vectors of the invention can be designed for expression of a scaffolded fusion polypeptide of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of scaffolded fusion polypeptide. A scaffolded fusion polypeptide can be expressed with a fusion vector or a non-fusion vector. Fusion vectors add a number of amino acids to a protein encoded therein, usually to the amino terminus of the recombinant protein. Such fusion vectors typically serve four purposes: 1) to increase expression of recombinant protein; 2) to increase the solubility of the recombinant protein; 3) to aid in the purification of the recombinant protein by acting as a ligand in affinity purification; and 4) to direct the cellular location of the recombinant protein (e.g. with signal peptides for secretion). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif.

(1990) 119–128). Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111–2118). Such alteration of nucleic acid sequences of the invention can be carried out by standard DNA synthesis techniques.

In another embodiment, the expression vector is a eukaryotic expression vector. Examples of eukaryotic expression vectors include fusion vectors similar to the prokaryotic fusion vectors discussed above, such as vectors that include a signal peptide fusion to direct secretion of the recombinant protein.

For instance, the expression vector is a yeast expression vector. Examples of vectors for expression in yeast *S. cerivisae* include pYepSec1 (Baldari et al., 1987, *EMBO J.* 6:229–234), pMFa (Kurjan and Herskowitz, 1982, *Cell* 30:933–943), pJRY88 (Schultz et al., 1987, *Gene* 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156–2165) and the pVL series (Lucklow and Summers, 1989, *Virology* 170:31–39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268–277), lymphoid-specific promoters (Calame and Eaton, 1988, *Adv. Immunol.* 43:235–275), in particular promoters of T cell receptors (Winoto andBaltimore, 1989, *EMBO J.* 8:729–733) and immunoglobulins (Banerji et al., 1983), Cell 33:729–740; Queen and Baltimore, 1983), Cell 33:741–748), neuron-specific promoters (e.g., the neurofilament promoter; Byrne and Ruddle, 1989, *Proc. Natl. Acad. Sci. USA* 86:5473–5477), pancreas-specific promoters (Edlund et al., 1985, *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the mouse hox promoters (Kessel and Gruss, 1990, *Science* 249:374–379) and the beta-fetoprotein promoter (Campes and Tilghman, 1989, *Genes Dev.* 3:537–546).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells). Host cells intended to be part of the invention include ones that comprise a nucleic acid molecule of the invention that has been engineered to be present within the host cell (e.g., as part of a vector), and ones that comprise nucleic acid regulatory sequences that have been engineered to be present in the host cell such that a nucleic acid molecule of the invention is expressed within the host cell.

Vector DNA can be introduced into prokaryotic or eukaryotic cells via conventional transformation or transfection techniques. The prokaryotic or eukaryotic cells can be transformed or transfected either stably or transiently. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, electroporation, viral infection or microinjection. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin andmethotrexate. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a polypeptide of the invention. Accordingly, the invention further provides methods for producing a scaffolded fusion polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

5.8 Methods of Producing Scaffolded Fusion Polypeptides

Isolated scaffolded fusion polypeptides of the present invention can be produced by a variety of means. For example, scaffolded fusion polypeptides of the invention that are entirely of gene-encoded amino acids may be produced recombinantly using any of the nucleic acids and expression vectors described above. Alternatively, all of the scaffolded fusion polypeptides of the invention may be produced by synthetic or semi-synthetic means.

For example, the polypeptide portions of a scaffolded fusion polypeptide can be produced by recombinant techniques or by standard chemical synthesis techniques such as those described by Merrifield, 1997, *Meth. Enzymol.* 289:3–13 (see also Williams et al., 1997, *Chemical Approaches to the Synthesis of Peptides and Proteins*, CRC Press, Boca Raton; Atherton & Sheppard, 1989, *Solid Phase Peptide Synthesis*, Oxford University Press, New York). The polypeptide portions of the scaffolded fusion polypeptide can then be linked together by standard synthetic techniques. For instance, peptide or polypeptide portions of the scaffolded fusion polypeptide can be linked together by standard techniques for forming amide linkages. Other portions of the scaffolded fusion protein, such as non-peptide and non-polypeptide linking molecules, can be linked to the appropriate portions of the scaffolded fusion protein also by standard synthetic techniques. The appropriate techniques will depend on the reactive groups of the portions of the scaffolded fusion polypeptide to be linked together, and will be readily apparent to those of skill in the art.

5.9 Uses

The scaffolded fusion polypeptides polypeptides of the invention can be used in virtually any assay or method in which the integral membrane proteins from which they were designed are useful. Owing to their solubility in membrane-free and detergent-free aqueous media, they find particular use in cell-free assays and methods. A few exemplary uses of the scaffolded fusion polypeptides of the invention are described in more detail below and are also exemplified in the working examples.

5.9.1 Methods of Raising an Immune Response

An scaffolded fusion polypeptide of the invention can be used as an antigen or immunogen to generate antibodies with specificity for a corresponding naturally occurring protein using standard techniques for polyclonal and monoclonal antibody preparation using standard techniques known to those of skill in the art. The scaffolded fusion polypeptide is optionally fused to a carrier protein, such as bovine serum albumin or keyhole limpet hemocyanin, to improve the immunogenicity of the scaffolded fusion polypeptide according to techniques well known to those of skill in the art.

An immunogen typically is used to prepare antibodies by immunizing a suitable subject, (e.g., rabbit, goat, mouse or other mammal). An appropriate immunogenic preparation can contain, for example, recombinantly expressed or chemically synthesized scaffolded fusion polypeptide. The preparation can further include an adjuvant, such as Freund's complete or incomplete adjuvant, or similar immunostimulatory agent.

5.9.2 Detecting Molecules that Interact with a Protein of Interest

The scaffolded fusion polypeptides of the invention can be used to identify a compound that binds to the integral membrane protein, or domain thereof, from which the scaffolded fusion polypeptide of the invention was designed. In general, such methods comprise contacting a test compound with a scaffolded fusion polypeptide of the invention for a time sufficient for the test compound to bind the polypeptide and assaying for the presence of bound test compound.

As used herein the term "selectively binds" refers to a compound (e.g., an antibody or small organic molecule) that binds to the native protein preferentially relative to other unrelated polypeptides. A compound selectively binds to the native protein preferentially relative polypeptide of the invention if it has at least a 10%, preferably at least a 25%, at least a 50%, at least a 75%, at least a 90%, at least a 95%, or at least a 100% higher affinity and/or avidity for the native protein than an unrelated polypeptide.

The polypeptides of the invention can be used to identify a compound that modulates the activity of the native protein. In general, such methods comprise measuring a biological activity of a scaffolded fusion polypeptide in the presence of a test compound, comparing the activity of the scaffolded fusion polypeptide to the biological activity of the scaffolded fusion polypeptide in the absence of the test compound, and identifying a test compound that alters the biological activity of the scaffolded fusion polypeptide. The compound can then be tested against the native protein according to standard techniques.

5.9.3 Phage Display Methods

In a particularly convenient embodiment of the invention, scaffolded fusion polypeptides are used in phage display methods. In phage display methods, scaffolded fusion polypeptides are displayed on the surface of phage particles according to standard techniques. For instance, DNA sequences encoding scaffolded fusion polypeptides are prepared according to the methods of the present invention and cloned into a phagemid vector (e.g., pCANTAB6 or pComb3HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII.

Phage that display a scaffolded fusion polypeptide with a desired property, function or structure can be selected according to techniques known to those of skill in the art. For instance, phage expressing a scaffolded fusion polypeptide that binds to a protein of interest can be selected or identified according to standard techniques such as ELISA or detection of radiolabeled molecules.

Examples of phage display methods that can be used to display the scaffolded fusion polypeptides of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280(1994); PCT application No. PCT/GB91/O1 134; PCT publications WO 90/02809; WO 91/10737; WO 92/01047; WO 92/18619; WO 93/11236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

5.9.4 Therapeutic Methods

The present invention provides for both prophylactic and therapeutic methods of treating a subject at risk of (or susceptible to) a disorder or having a disorder associated with aberrant expression or activity of an integral membrane protein or a molecule that interacts with an integral membrane protein. In particular, the scaffolded fusion polypeptide corresponding to the ECD of CCR5 can be used to treat or prevent HIV infection in a subject.

A scaffolded fusion polypeptide can be administered in a composition comprising the fusion polypeptide to treat or prevent the disorder. In an alternative embodiment, a composition comprising a nucleic acid encoding a scaffolded fusion polypeptide can be administered treat or prevent the disorder. In this embodiment, cells of the subject take up and express the nucleic acid thereby producing the therapeutic scaffolded fusion polypeptide.

5.9.4.1 Compositions

The pharmaceutical compositions of the invention include compositions which comprise scaffolded fusion polypeptides and compositions which comprise nucleic acids that encode scaffolded fusion polypeptides. These scaffolded fusion polypeptides and nucleic acids are also referred to herein as "active compounds" or "active agents."

The compositions of the invention typically comprise an active agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

5.9.4.2 Effective Dosages

The agents of the invention, or compositions thereof, will generally be used in an amount effective to achieve the intended purpose. Of course, it is to be understood that the amount used will depend on the particular application.

For example, for use as an antiviral entity, a therapeutically effective amount of an agent, or composition thereof, is applied or administered to an animal or human in need thereof. By therapeutically effective amount is meant an amount of peptide or composition that inhibits the growth or spread of a viral infection in the subject. The actual therapeutically effective amount will depend on a particular application. An ordinarily skilled artisan will be able to determine therapeutically effective amounts of particular agents for particular applications without undue experimentation using, for example, the in vitro assays for the particular disease target known to those of skill in the art.

For use to treat or prevent diseases related to the function or abnormal expression of an integral membrane protein, the agents of the invention, or compositions thereof, are administered or applied in a therapeutically effective amount. By therapeutically effective amount is meant an amount effective to ameliorate the symptoms of, or ameliorate, treat or prevent diseases related to the function or abnormal expression of an integral membrane protein. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating agent concentration range that includes the 150 as determined in cell culture (i.e., the concentration of the agent that is lethal to 50% of a cell culture), the MIC, as determined in cell culture (i.e., the minimal inhibitory concentration for growth) or the $I_{100}$ as determined in cell culture (i.e., the concentration of the agent that is lethal to 100% of a cell culture). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

The amount of agent administered will, of course, be dependent on the subject being treated, on the subject's weight, the severity of the affunction, the manner of administration and the judgment of the prescribing physician.

The therapy may be repeated intermittently. The therapy may be provided alone or in combination with other drugs, such as for example other antiviral entities or other pharmaceutically effective entities.

5.9.4.3 Toxicity

Preferably, a therapeutically effective dose of the agents described herein will provide therapeutic benefit without causing substantial toxicity.

Toxicity of the agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Agents which exhibit high therapeutic indices are preferred. The data obtained from these cell culture assays and animal studies can be used in formulating a dosage range that is not toxic for use in human. The dosage of the agents described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch.1, p.1).

5.9.4.4 Gene Therapy

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

5.9.4.5 Therapeutic Methods

In one aspect, the invention provides a method for preventing in a subject, a disease or condition associated with an aberrant expression or activity of an integral membrane protein or a molecule that interacts with an integral membrane protein, by administering to the subject a composition comprising a scaffolded fusion polypeptide of the invention. In another aspect, the present invention provides a method of treating or preventing such a disease or condition by administering to the subject composition comprising a nucleic acid encoding a scaffolded fusion polypeptide of the invention. Administration of a prophylactic agent can occur prior to the manifestation of symptoms characteristic of the aberrancy, such that a disease or disorder is prevented or, alternatively, delayed in its progression.

Another aspect of the invention pertains to methods of modulating expression or activity of an integral membrane protein or a molecule that interacts with an integral membrane protein. The modulatory method of the invention involves contacting a cell with an agent that modulates one or more of the activities of the integral membrane protein or molecule that interacts with an integral membrane protein. An agent that modulates activity can be an agent as described herein, such as a nucleic acid or a scaffolded fusion polypeptide. In one embodiment, the agent stimulates one or more of the biological activities of the polypeptide. Examples of such stimulatory agents include a polypeptide of the invention and a nucleic acid molecule encoding the polypeptide of the invention that has been introduced into a cell. In another embodiment, the agent inhibits one or more of the biological activities of the polypeptide of the invention. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of an integral membrane protein or a molecule that interacts with an integral membrane protein. In one embodiment, the method involves administering an agent (e.g., an agent identified by a screening assay described herein), or combination of agents that modulates (e.g., upregulates or downregulates) expression or activity. In another embodiment, the method involves administering a polypeptide of the invention or a nucleic acid molecule of the invention as therapy to compensate for reduced or aberrant expression or activity of the integral membrane protein or a molecule that interacts with an integral membrane protein.

The invention having been described, the following examples are intended to illustrate, and not limit, this invention.

6. EXAMPLES

6.1 Preparation of Vector for Expression of a CCR5 Scaffolded Fusion Polypeptide This example describes the preparation of a vector that encodes a scaffolded fusion polypeptide corresponding to the ECD of the 7TM CCR5.

A nucleic acid encoding the polypeptide of SEQ ID NO:10 was prepared by standard recombinant techniques. In brief, eight overlapping oligonucleotides were synthesized and are presented in Table 3, below. Together, the oligonucleotides correspond to a nucleic acid that encodes the polypeptide of SEQ ID NO:10 operably linked to a T7 promoter.

Four overlapping oligonucleotides (66732, 66733, 66734 and 66735) were designed to synthesize a nucleic acid (N-L1) encoding portions of SEQ ID NO:10. The nucleic acid N-L1 included two termination codons at the end of its coding sequence and was flanked by a BamHI restriction site at the 5' end and a Nde1 restriction site at the 3' end. The four overlapping oligonucleotides were mixed and amplified by PCR. The resulting first nucleic acid (N-L1) was cloned into the bacterial vector pE4. The DNA sequence of N-L1 was confirmed. The nucleic acid N-L1 was amplified by PCR using oligonucleotide 68133 (to remove the termination codons and the 3' restriction site) and oligonucleotide 68132 to yield nucleic acid N-L1'. Excess oligonucleotides were removed using a Qiagen PCR clean-up kit.

Four more overlapping oligonucleotides (66974, 66978, 66979 and 66980) were designed to synthesize a nucleic acid (L2–L3) encoding the remaining portions of SEQ ID NO:10. The nucleic acid L2–L3 includes two termination codons at the end of its coding sequence and a Nde1 restriction site at the 3' end. The overlapping oligonucleotides were mixed and amplified by PCR to yield nucleic acid L2–L3. Excess oligonucleotides were removed using a Qiagen PCR clean-up kit.

Nucleic acid N-L3 was assembled by site overlap extension PCR with nucleic acid N-L1', nucleic acid L2–L3 and oligonucleotides 68132 and 66983. Nucleic acid N-L3 included two termination codons at the end of its coding sequence and was flanked by a BamHI restriction site at the 5' end and a Nde1 restriction site at the 3' end. Nucleic acid N-L3 was gel purified and cloned into a pHE4 vector. The DNA sequence of N-L3 showed a single nucleotide mutation.

Nucleic acid N-L3' was synthesized by amplifying nucleic acid N-L3 by PCR with oligonucleotide 68355 and oligonucleotide 69444. Oligonucleotide 68355 introduces a BamHI restriction site and a baculoviral Kozak sequence at the 5' end of N-L3'. Oligonucleotide 69444 corrects the mutation in N-L3 and introduces an XbaI site at the 3' end of N-L3'. Nucleic acid N-L3' was cleaned with a Qiagen PCR clean-up kit, and cloned into a pBlueBac4.5 vector. The sequence of N-L3' in the pBlueBac4.5 vector was confirmed.

Expression of N-L3' in Sf9 cells with metabolic labeling showed that a polypeptide of the correct size was synthesized and retained within the cells.

TABLE 3

Oligonucleotides For the Synthesis of the
CCR5 Zinc Finger Scaffolded fusion polypeptide

| | | |
|---|---|---|
| 66732 | GATCTGTAATACGACTCACTATAGGGCACCATATGGACTACCAGG TTTCTTCTCCGATCTACGACATCAACT | (SEQ ID NO:17) |
| 66733 | GCAGCGATCTGTTTAACGTTGATTTTCTGGCACGGTTCAGAGGTG TAGTAGTTGATGTCGTAGATCGGAGAA | (SEQ ID NO:18) |
| 66734 | AATCAACGTTAAACAGATCGCTGCTTACAAATGCGGTCTGTGCGC TGCTGCTCAGTGGGACTTCGGTAACAC | (SEQ ID NO:19) |
| 66735 | GGATCCGGATCCTTATTAGTGGTGGTGGTGACCGTGACACGCTG GTGCTGGCACATGGTGTTACCGAAGTCCCACTGA | (SEQ ID NO:20) |
| 66974 | GTTCACGGTCACCACCACCACTCTTACAAATGCGGTCTGTGCACC CGTTCTCAGAAAGAAGGTCTGCACTACACCTGCTCTT | (SEQ ID NO:21) |
| 66978 | GGTGGATTTTCAGGGTCTGGAAGTTTTTCCAGAACTGGTACTGAG AGTACGGGAAGTGAGAAGAGCAGGTGTAGTGCAGACC | (SEQ ID NO:22) |
| 66979 | TTCCAGACCCTGAAAATCCACCAGCGTGTTCACCATCACCATTCT TACAAATGCGGTCTGTGCCAGGAATTCTTCGGTCTGA | (SEQ ID NO:23) |
| 66980 | GGATCCGGATCCTTATTAAGCAGCGTGACACGCTGGTGACCGTC CAGACGGTTAGAGAGAGCAGTTGTTCAGACCGAGATTCCTG GCA | (SEQ ID NO:24) |
| 68132 | CATATGCATATGGACTACCAGGTTTCTTCTCCG | (SEQ ID NO:25) |
| 68133 | GAGTGGTGGTGGTGACCGTGAAC | (SEQ ID NO:26) |
| 68355 | GGATCCGGATCCATAAATATGGACTACCAGGTTTCTTCTCCG | (SEQ ID NO:27) |

TABLE 3-continued

Oligonucleotides For the Synthesis of the
CCR5 Zinc Finger Scaffolded fusion polypeptide

| | | |
|---|---|---|
| 68356 | GGATCCGGATCCATAAATATGAAGGTCTCCGTGGCTGCCCTCTCC TGCCTCATGCTTGTTACTGCCCTTGGATCGATGGACTACAGGTT TCTTCTCCG | (SEQ ID NO:28) |
| 69444 | TCTAGATCTAGATTATTAAGCAGCGTGAACACGCTGGTGACCGTC CAG | (SEQ ID NO:29) |
| 71470 | GGTACCGGTACCTTATTAAGCAGCGTGAACACGCTGGTGAC | (SEQ ID NO:30) |

6.2 Preparation of Vector for Expression of a CCR5 Scaffolded Fusion Polypeptide This example describes the preparation of a vector that encodes a scaffolded fusion polypeptide corresponding to the ECD of the 7TM CCR5. The scaffolded fusion polypeptide of this example (SEQ ID NO:31, Table 4) includes the signal sequence MKVSVAALSCLMLVTALGS (SEQ ID NO:32) for expression and secretion in a baculoviral expression system.

TABLE 4

| Amino Acid Sequence of CCR5 Scaffolded Fusion Polypeptide with Signal Sequence |
|---|
| MKVSVAALSCLMLVTALGS MDYQVSSPTYDTNYYTSEPCQKINVKQIAA YKCGLC (SEQ ID NO:31) |
| AAAQWDFGNTMCQ HQRVH GHHHHS YKCGLC |
| TRSQKEGLHYTCSSHFPYSQYQFWKNFQTLKI HQRVH GGGGS YKCGLC |
| QEFFGLNNCSSSNRLDG HQRVH AA |

Nucleic acid N-L3" was synthesized by amplifying nucleic acid N-L3 (Example 1) by PCR with oligonucleotide 68356 and oligonucleotide 69444. Oligonucleotide 68356 introduces a BamHI restriction site, a baculoviral Kozak sequence and a sequence encoding the signal sequence SEQ ID NO:32 at the 5' end of N-L3". Oligonucleotide 69444 corrects the mutation in N-L3 and introduces an XbaI site at the 3' end of N-L3". Nucleic acid N-L3" was cleaned with a Qiagen PCR clean-up kit, and cloned into a pBlueBac4.5 vector. The sequence of N-L3" in the pBlueBac4.5 vector was confirmed.

Expression of N-13" in Sf9 cells with metabolic labeling showed that a polypeptide of the correct size was synthesized and retained within the cells.

6.3 Expression and Immunoprecipitation of the CCR5 Scaffolded Fusion Polypeptide This example describes the expression of the CCR5 scaffolded fusion polypeptide SEQ ID NO:10 and its immunoprecipitation with antibodies specific for the correct native conformation of CCR5. Remarkably, immunoprecipitation experiments indicated that at least a fraction of the expressed CCR5 scaffolded fusion polypeptides adopted a native CCR5 conformation.

Nucleic acid N-L3'" was synthesized by amplifying nucleic acid N-L3' (Example 1) by PCR with oligonucleotide 68132 and oligonucleotide 71740. Oligonucleotide 68132 introduces a NdeI restriction site, removes the BamHI site and the baculoviral Kozak sequence while introducing a NdeI site at the 5' end of N-L3'". Oligonucleotide 71740 replaces the XbaI site with an Asp718 site at the 3' end of N-L3'". Nucleic acid N-L3" was cleaned with a Qiagen PCR clean-up kit, and cloned into a pHE4 vector. The sequence of N-L3'" was confirmed.

The CCR5 scaffolded fusion polypeptide was expressed in vitro from the vector of Example 1 in a transcription-coupled translation system (Promega) according to standard techniques and in a bacterial expression system.

The antibody FAB182B (R&D Systems) can be used to distinguish a properly folded CCR5 molecule from linear fragments of CCR5. The FAB182B antibody recognizes a portion of loop 2 of the ECD of the native CCR5 receptor; it does not recognize linear CCR5 epitopes. Lee et al., 1999, *J. Biol. Chem.* 274:9617–9626. The antibody 2D7 (Pharmingen cat. no. 36465X) has specificity for the first half of loop 2 of the ECD of the native CCR5 receptor. Antibodies MAB1801 and MAB1802 (R&D Systems) both recognize linear epitopes of the CCR5 receptor.

Immunoprecipitation experiments were carried out according to standard techniques. In brief, aliquots of the reticulocyte lysate were immunoprecipitated in PBS, 0.05% Triton X-100, with 5 μg MAB182B, 5 μg 2D7, or a mixture of 5 μg MAB1801 and 5 μg MAB 1802. The immunoprecipitations were performed overnight at 4° C. On the following day, complexes were bound with either 20 μL POROS ProteinA beads or 20 μL streptavidin beads, as appropriate, by incubation at room temperature for 3 hours. Complexes were then pelleted by centrifugation for 30 sec in an Eppendorf microfuge, and the unbound material was removed. The pellets were washed three times and then suspended in 100 μL 5× SDS (60 mM Tris-HCl pH 6.8, 25% glycerol, 2% SDS, 14.4 mM 2-mercaptoethanol and 0.1% bromophenol blue). The recovered proteins were analyzed by SDS-PAGE followed by autoradiography.

Significantly, fractions of the CCR5 scaffolded fusion polypeptide were specifically immunoprecipitated by both the B182B antibody and the 2D7 antibody. A portion of the CCR5 scaffolded fusion polypeptide therefore adopted a conformation close enough to that of the native CCR5 receptor ECD for antibody recognition and immunoprecipitation.

Various embodiments of the invention have been described. The descriptions and examples are intended to be illustrative of the invention and not limiting. Indeed, it will be apparent to those of skill in the art that modifications may be made to the various embodiments of the invention described without departing from the spirit of the invention or scope of the appended claims set forth below.

All references cited herein are hereby incorporated by reference in their entireties.

What is claimed is:

1. A soluble scaffolded fusion polypeptide comprising the amino acid sequence of SEQ ID NO:10.

2. The scaffolded fusion polypeptide of claim 1 comprising the amino acid sequence of SEQ ID NO:31.

3. A polypeptide produced by a method comprising:
   (a) expressing from a host cell the polypeptide of claim 1; and
   (b) recovering said polypeptide.

* * * * *

SEQUENCE LISTING

```
<160> NUMBER OF SEQ ID NOS: 32

<210> SEQ ID NO 1
<211> LENGTH: 8
<212> TYPE: PRT
<213> ORGANISM: Homo sapiens

<400> SEQUENCE: 1

Glu Phe Leu Ile Val Ile Lys Ser
 1               5

<210> SEQ ID NO 2
<211> LENGTH: 27
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa equals either the naturally occurring L-
      amino acid Phe or Tyr
<220> FEATURE:
<221> NAME/KEY: MISC_FEATURE
<222> LOCATION: (2)..(2)
<223> OTHER INFORMATION: Xaa equals any of the naturally occurring L-
      amino acids
<220> FEATURE:
<221> NAME/KEY: MISC_FEATURE
<222> LOCATION: (4)..(7)
<223> OTHER INFORMATION: Xaa equals any of the naturally occurring L-
      amino acids, one or two residues may be missing
<220> FEATURE:
<221> NAME/KEY: MISC_FEATURE
<222> LOCATION: (9)..(9)
<223> OTHER INFORMATION: Xaa equals any of the naturally occurring L-
      amino acids
<220> FEATURE:
<221> NAME/KEY: MISC_FEATURE
<222> LOCATION: (10)..(10)
<223> OTHER INFORMATION: Xaa equals any of the naturally occurring L-
      amino acids
<220> FEATURE:
<221> NAME/KEY: MISC_FEATURE
<222> LOCATION: (11)..(11)
<223> OTHER INFORMATION: Xaa equals any of the naturally occurring L-
      amino acids
<220> FEATURE:
<221> NAME/KEY: MISC_FEATURE
<222> LOCATION: (13)..(13)
<223> OTHER INFORMATION: Xaa equals any of the naturally occurring L-
      amino acids
<220> FEATURE:
<221> NAME/KEY: MISC_FEATURE
<222> LOCATION: (14)..(14)
<223> OTHER INFORMATION: Xaa equals any of the naturally occurring L-
      amino acids
<220> FEATURE:
<221> NAME/KEY: MISC_FEATURE
<222> LOCATION: (15)..(15)
<223> OTHER INFORMATION: Xaa equals any of the naturally occurring L-
      amino acids
<220> FEATURE:
<221> NAME/KEY: MISC_FEATURE
<222> LOCATION: (16)..(16)
<223> OTHER INFORMATION: Xaa equals any of the naturally occurring L-
      amino acids
<220> FEATURE:
<221> NAME/KEY: MISC_FEATURE
<222> LOCATION: (17)..(17)
<223> OTHER INFORMATION: Xaa equals any of the naturally occurring L-
      amino acids
```

```
<220> FEATURE:
<221> NAME/KEY: MISC_FEATURE
<222> LOCATION: (19)..(19)
<223> OTHER INFORMATION: Xaa equals any of the naturally occurring L-
      amino acids
<220> FEATURE:
<221> NAME/KEY: MISC_FEATURE
<222> LOCATION: (20)..(20)
<223> OTHER INFORMATION: Xaa equals any of the naturally occurring L-
      amino acids
<220> FEATURE:
<221> NAME/KEY: MISC_FEATURE
<222> LOCATION: (22)..(26)
<223> OTHER INFORMATION: Xaa equals any of the naturally occurring L-
      amino acids, one or two residues may be missing.

<400> SEQUENCE: 2

Xaa Xaa Cys Xaa Xaa Xaa Xaa Cys Xaa Xaa Xaa Phe Xaa Xaa Xaa Xaa Xaa Leu
 1               5                  10                  15

Xaa Xaa His Xaa Xaa Xaa Xaa Xaa His
     20                  25

<210> SEQ ID NO 3
<211> LENGTH: 10
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa equals any of the naturally occurring L-
      amino acids, one or two residues may be missing

<400> SEQUENCE: 3

Cys Pro Glu Cys Xaa His Gln Arg Thr His
 1               5                  10

<210> SEQ ID NO 4
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa equals either the naturally occurring L-
      amino acid Phe or Tyr
<220> FEATURE:
<221> NAME/KEY: MISC_FEATURE
<222> LOCATION: (2)..(2)
<223> OTHER INFORMATION: Xaa equals any of the naturally occurring L-
      amino acids
<220> FEATURE:
<221> NAME/KEY: MISC_FEATURE
<222> LOCATION: (4)..(7)
<223> OTHER INFORMATION: Xaa equals any of the naturally occurring L-
      amino acids, one or two residues may be missing

<400> SEQUENCE: 4

Xaa Xaa Cys Xaa Xaa Xaa Xaa Cys
 1               5

<210> SEQ ID NO 5
<211> LENGTH: 7
<212> TYPE: PRT
<213> ORGANISM: Homo sapiens
<220> FEATURE:
<221> NAME/KEY: MISC_FEATURE
<222> LOCATION: (2)..(6)
<223> OTHER INFORMATION: Xaa equals any of the naturally occurring L-
      amino acids, one or two residues may be missing

<400> SEQUENCE: 5
```

```
His Xaa Xaa Xaa Xaa Xaa His
 1               5
```

<210> SEQ ID NO 6
<211> LENGTH: 6
<212> TYPE: PRT
<213> ORGANISM: Homo sapiens

<400> SEQUENCE: 6

```
Tyr Lys Cys Gly Leu Cys
 1               5
```

<210> SEQ ID NO 7
<211> LENGTH: 5
<212> TYPE: PRT
<213> ORGANISM: Homo sapiens

<400> SEQUENCE: 7

```
His Gln Arg Val His
 1               5
```

<210> SEQ ID NO 8
<211> LENGTH: 7
<212> TYPE: PRT
<213> ORGANISM: Homo sapiens

<400> SEQUENCE: 8

```
Thr Gly Glu Lys Pro Tyr Lys
 1               5
```

<210> SEQ ID NO 9
<211> LENGTH: 209
<212> TYPE: PRT
<213> ORGANISM: Homo sapiens

<400> SEQUENCE: 9

```
Met Asp Tyr Val Ser Ser Tyr Asp Asn Tyr Tyr Thr Ser Cys Lys Asn
 1               5                  10                  15

Val Lys Ala Ala Arg Tyr Ser Val Gly Val Gly Asn Met Val Asn Cys
                20                  25                  30

Lys Arg Lys Ser Met Thr Asp Tyr Asn Ala Ser Asp Thr Val Trp Ala
            35                  40                  45

His Tyr Ala Ala Ala Trp Asp Gly Asn Thr Met Cys Thr Gly Tyr Gly
        50                  55                  60

Ser Gly Thr Asp Arg Tyr Ala Val Val His Ala Val Ala Lys Ala Arg
 65                  70                  75                  80

Thr Val Thr Gly Val Val Thr Ser Val Thr Trp Val Val Ala Val Ala
                85                  90                  95

Ser Gly Thr Arg Ser Lys Gly His Tyr Thr Cys Ser Ser His Tyr Ser
                100                 105                 110

Tyr Trp Lys Asn Thr Lys Val Gly Val Met Val Cys Tyr Ser Gly
            115                 120                 125

Lys Thr Arg Cys Arg Asn Lys Lys Arg His Arg Ala Val Arg Thr Met
        130                 135                 140

Val Tyr Trp Ala Tyr Asn Val Asn Thr Gly Asn Asn Cys Ser Ser Ser
145                 150                 155                 160

Asn Arg Asp Ala Met Val Thr Gly Met Thr His Cys Asn Tyr
                165                 170                 175

Ala Val Gly Lys Arg Asn Tyr Val Lys His Ala Lys Arg Cys Lys Cys
            180                 185                 190
```

```
Cys Ser Ala Arg Ala Ser Ser Val Tyr Thr Arg Ser Thr Gly Ser Val
            195                 200                 205

Gly

<210> SEQ ID NO 10
<211> LENGTH: 138
<212> TYPE: PRT
<213> ORGANISM: Homo sapiens

<400> SEQUENCE: 10

Met Asp Tyr Gln Val Ser Ser Pro Ile Tyr Asp Ile Asn Tyr Tyr Thr
  1               5                  10                  15

Ser Glu Pro Cys Gln Lys Ile Asn Val Lys Gln Ile Ala Ala Tyr Lys
             20                  25                  30

Cys Gly Leu Cys Ala Ala Gln Trp Asp Phe Gly Asn Thr Met Cys
         35                  40                  45

Gln His Gln Arg Val His Gly His His His Ser Tyr Lys Cys Gly
     50                  55                  60

Leu Cys Thr Arg Ser Gln Lys Glu Gly Leu His Tyr Thr Cys Ser Ser
 65                  70                  75                  80

His Phe Pro Tyr Ser Gln Tyr Gln Phe Trp Lys Asn Phe Gln Thr Leu
                 85                  90                  95

Lys Ile His Gln Arg Val His Gly Gly Gly Ser Tyr Lys Cys Gly
             100                 105                 110

Leu Cys Gln Glu Phe Phe Gly Leu Asn Asn Cys Ser Ser Asn Arg
         115                 120                 125

Leu Asp Gly His Gln Arg Val His Ala Ala
         130                 135

<210> SEQ ID NO 11
<211> LENGTH: 30
<212> TYPE: PRT
<213> ORGANISM: Homo sapiens

<400> SEQUENCE: 11

Met Asp Tyr Gln Val Ser Ser Pro Ile Tyr Asp Ile Asn Tyr Tyr Thr
  1               5                  10                  15

Ser Glu Pro Cys Gln Lys Ile Asn Val Lys Gln Ile Ala Ala
             20                  25                  30

<210> SEQ ID NO 12
<211> LENGTH: 13
<212> TYPE: PRT
<213> ORGANISM: Homo sapiens

<400> SEQUENCE: 12

Ala Ala Ala Gln Trp Asp Phe Gly Asn Thr Met Cys Gln
  1               5                  10

<210> SEQ ID NO 13
<211> LENGTH: 32
<212> TYPE: PRT
<213> ORGANISM: Homo sapiens

<400> SEQUENCE: 13

Thr Arg Ser Gln Lys Glu Gly Leu His Tyr Thr Cys Ser Ser His Phe
  1               5                  10                  15

Pro Tyr Ser Gln Tyr Gln Phe Trp Lys Asn Phe Gln Thr Leu Lys Ile
             20                  25                  30
```

<210> SEQ ID NO 14
<211> LENGTH: 17
<212> TYPE: PRT
<213> ORGANISM: Homo sapiens

<400> SEQUENCE: 14

Gln Glu Phe Phe Gly Leu Asn Asn Cys Ser Ser Ser Asn Arg Leu Asp
 1               5                  10                  15

Gly

<210> SEQ ID NO 15
<211> LENGTH: 6
<212> TYPE: PRT
<213> ORGANISM: Homo sapiens

<400> SEQUENCE: 15

Gly His His His His Ser
 1               5

<210> SEQ ID NO 16
<211> LENGTH: 5
<212> TYPE: PRT
<213> ORGANISM: Homo sapiens

<400> SEQUENCE: 16

Gly Gly Gly Gly Ser
 1               5

<210> SEQ ID NO 17
<211> LENGTH: 72
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 17
gatctgtaat acgactcact atagggcacc atatggacta ccaggtttct tctccgatct      60
acgacatcaa ct                                                         72

<210> SEQ ID NO 18
<211> LENGTH: 72
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 18
gcagcgatct gtttaacgtt gattttctgg cacggttcag aggtgtagta gttgatgtcg      60
tagatcggag aa                                                         72

<210> SEQ ID NO 19
<211> LENGTH: 72
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 19
aatcaacgtt aaacagatcg ctgcttacaa atgcggtctg tgcgctgctg ctcagtggga      60

-continued cttcggtaac ac                                                72

<210> SEQ ID NO 20
<211> LENGTH: 79
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 20
ggatccggat ccttattagt ggtggtggtg accgtgaaca cgctggtgct ggcacatggt    60
gttaccgaag tcccactga                                                79

<210> SEQ ID NO 21
<211> LENGTH: 82
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 21
gttcacggtc accaccacca ctcttacaaa tgcggtctgt gcaccgttc tcagaaagaa     60 ggtctgcact acacctgctc tt                                            82

<210> SEQ ID NO 22
<211> LENGTH: 82
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 22
ggtggatttt cagggtctgg aagttttcc agaactggta ctgagagtac gggaagtgag     60
aagagcaggt gtagtgcaga cc                                            82

<210> SEQ ID NO 23
<211> LENGTH: 82
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 23
ttccagaccc tgaaaatcca ccagcgtgtt caccatcacc attcttacaa atgcggtctg    60
tgccaggaat tcttcggtct ga                                            82

<210> SEQ ID NO 24
<211> LENGTH: 93
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 24
ggatccggat ccttattaag cagcgtgaac acgctggtga ccgtccagac ggttagaaga    60
agagcagttg ttcagaccga agaattcctg gca                                93

<210> SEQ ID NO 25

```
<211> LENGTH: 33
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 25
catatgcata tggactacca ggtttcttct ccg                                33

<210> SEQ ID NO 26
<211> LENGTH: 23
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 26
gagtggtggt ggtgaccgtg aac                                          23

<210> SEQ ID NO 27
<211> LENGTH: 42
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 27
ggatccggat ccataaatat ggactaccag gtttcttctc cg                     42

<210> SEQ ID NO 28
<211> LENGTH: 99
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 28
ggatccggat ccataaatat gaaggtctcc gtggctgccc tctcctgcct catgcttgtt  60
actgcccttg gatcgatgga ctaccaggtt tcttctccg                         99

<210> SEQ ID NO 29
<211> LENGTH: 48
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 29
tctagatcta gattattaag cagcgtgaac acgctggtga ccgtccag               48

<210> SEQ ID NO 30
<211> LENGTH: 41
<212> TYPE: DNA
<213> ORGANISM: Artificial sequence
<220> FEATURE:
<223> OTHER INFORMATION: Synthetic oligonucleotides used to join DNA
      fragments

<400> SEQUENCE: 30
ggtaccggta ccttattaag cagcgtgaac acgctggtga c                      41
```

```
<210> SEQ ID NO 31
<211> LENGTH: 157
<212> TYPE: PRT
<213> ORGANISM: Homo sapiens

<400> SEQUENCE: 31

Met Lys Val Ser Val Ala Ala Leu Ser Cys Leu Met Leu Val Thr Ala
 1               5                  10                  15

Leu Gly Ser Met Asp Tyr Gln Val Ser Ser Pro Ile Tyr Asp Ile Asn
                20                  25                  30

Tyr Tyr Thr Ser Glu Pro Cys Gln Lys Ile Asn Val Lys Gln Ile Ala
            35                  40                  45

Ala Tyr Lys Cys Gly Leu Cys Ala Ala Ala Gln Trp Asp Phe Gly Asn
    50                  55                  60

Thr Met Cys Gln His Gln Arg Val His Gly His His His Ser Tyr
 65                  70                  75                  80

Lys Cys Gly Leu Cys Thr Arg Ser Gln Lys Glu Gly Leu His Tyr Thr
                85                  90                  95

Cys Ser Ser His Phe Pro Tyr Ser Gln Tyr Gln Phe Trp Lys Asn Phe
                100                 105                 110

Gln Thr Leu Lys Ile His Gln Arg Val His Gly Gly Gly Gly Ser Tyr
            115                 120                 125

Lys Cys Gly Leu Cys Gln Glu Phe Phe Gly Leu Asn Asn Cys Ser Ser
    130                 135                 140

Ser Asn Arg Leu Asp Gly His Gln Arg Val His Ala Ala
145                 150                 155

<210> SEQ ID NO 32
<211> LENGTH: 19
<212> TYPE: PRT
<213> ORGANISM: Homo sapiens

<400> SEQUENCE: 32

Met Lys Val Ser Val Ala Ala Leu Ser Cys Leu Met Leu Val Thr Ala
 1               5                  10                  15

Leu Gly Ser
```